(12) United States Patent
Welch et al.

(10) Patent No.: US 11,963,736 B2
(45) Date of Patent: Apr. 23, 2024

(54) WIRELESS PATIENT MONITORING SYSTEM

(71) Applicant: MASIMO CORPORATION, Irvine, CA (US)

(72) Inventors: James P. Welch, Mission Viejo, CA (US); Massi Joe E. Kiani, Laguna Niguel, CA (US); Gregory A. Olsen, Trabuco Canyon, CA (US); Nicholas Evan Barker, Laguna Beach, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 17/138,595

(22) Filed: Dec. 30, 2020

(65) Prior Publication Data

US 2021/0161442 A1    Jun. 3, 2021

Related U.S. Application Data

(63) Continuation of application No. 13/010,653, filed on Jan. 20, 2011, now abandoned, which is a
(Continued)

(51) Int. Cl.
*A61B 5/0205* (2006.01)
*A61B 5/00* (2006.01)
*A61B 5/1455* (2006.01)

(52) U.S. Cl.
CPC ............ *A61B 5/002* (2013.01); *A61B 5/0017* (2013.01); *A61B 5/0205* (2013.01);
(Continued)

(58) Field of Classification Search
CPC ............ A61B 5/14551; A61B 5/14552; A61B 5/0017; A61B 5/002; A61B 5/6826;
(Continued)

(56) References Cited

U.S. PATENT DOCUMENTS

| 4,960,128 A | 10/1990 | Gordon et al. |
| 4,964,408 A | 10/1990 | Hink et al. |

(Continued)

FOREIGN PATENT DOCUMENTS

| EP | 0 735 499 | 10/1996 |
| EP | 1 110 503 | 6/2001 |

(Continued)

OTHER PUBLICATIONS

US 2022/0192529 A1, 06/2022, Al-Ali et al. (withdrawn)
(Continued)

*Primary Examiner* — Daniel L Cerioni
(74) *Attorney, Agent, or Firm* — Knobbe, Martens, Olson & Bear LLP

(57) ABSTRACT

A device for obtaining physiological information of a medical patient and wirelessly transmitting the obtained physiological information to a wireless receiver. The device can include a blood pressure device that can be coupled to a medical patient and a wireless transceiver electrically coupled with the blood pressure device. The wireless transceiver can wirelessly transmit blood pressure data received by the blood pressure device and physiological data received from one or more physiological sensors coupled to the blood pressure device.

14 Claims, 11 Drawing Sheets

Related U.S. Application Data continuation-in-part of application No. 12/840,209, filed on Jul. 20, 2010, now abandoned.

(60) Provisional application No. 61/350,673, filed on Jun. 2, 2010, provisional application No. 61/290,436, filed on Dec. 28, 2009, provisional application No. 61/259,037, filed on Nov. 6, 2009, provisional application No. 61/226,996, filed on Jul. 20, 2009.

(52) U.S. Cl.
CPC ........ *A61B 5/14551* (2013.01); *A61B 5/6826* (2013.01); *A61B 5/7225* (2013.01); *A61B 5/742* (2013.01); *A61B 5/7285* (2013.01); *A61B 2562/0233* (2013.01); *A61B 2562/222* (2013.01)

(58) Field of Classification Search
CPC ......... A61B 5/7225; A61B 5/72; A61B 5/742; A61B 7/02416; A61B 2562/0233
USPC ....................................................... 600/323
See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,307,263 A | 4/1994 | Brown |
| 5,309,918 A | 5/1994 | Schraag |
| 5,319,355 A | 6/1994 | Russek |
| 5,337,744 A | 8/1994 | Branigan |
| 5,341,805 A | 8/1994 | Stavridi et al. |
| 5,358,519 A | 10/1994 | Grandjean |
| D353,195 S | 12/1994 | Savage et al. |
| D353,196 S | 12/1994 | Savage et al. |
| 5,375,604 A | 12/1994 | Kelly et al. |
| 5,377,676 A | 1/1995 | Vari et al. |
| 5,390,238 A | 2/1995 | Kirk et al. |
| 5,406,952 A | 4/1995 | Barnes et al. |
| D357,982 S | 5/1995 | Dahl et al. |
| 5,420,606 A | 5/1995 | Begum et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,477,146 A | 12/1995 | Jones |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,537,289 A | 7/1996 | Dahl |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,953 A | 6/1997 | Bishop et al. |
| 5,645,440 A | 7/1997 | Tobler et al. |
| 5,651,368 A | 7/1997 | Napolitano |
| 5,671,914 A | 9/1997 | Kalkhoran et al. |
| 5,685,299 A | 11/1997 | Diab et al. |
| 5,685,314 A | 11/1997 | Geheb et al. |
| 5,687,717 A | 11/1997 | Halpern et al. |
| 5,687,732 A | 11/1997 | Inagaki |
| 5,694,020 A | 12/1997 | Lang et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,772,586 A | 6/1998 | Heinonen et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,813,403 A | 9/1998 | Soller et al. |
| 5,822,546 A | 10/1998 | George |
| 5,823,950 A | 10/1998 | Diab et al. |
| 5,829,723 A | 11/1998 | Brunner |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,876,351 A | 3/1999 | Rohde |
| 5,885,214 A | 3/1999 | Monroe et al. |
| 5,890,929 A | 4/1999 | Mills et al. |
| 5,895,359 A | 4/1999 | Peel, III |
| 5,904,654 A | 5/1999 | Wohltmann et al. |
| 5,910,139 A | 6/1999 | Cochran et al. |
| 5,919,134 A | 7/1999 | Diab |
| 5,931,791 A | 8/1999 | Saltzstein et al. |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,006,119 A | 12/1999 | Soller et al. |
| 6,010,937 A | 1/2000 | Karam et al. |
| 6,011,986 A | 1/2000 | Diab et al. |
| 6,018,673 A | 1/2000 | Chin et al. |
| 6,027,452 A | 2/2000 | Flaherty et al. |
| 6,036,642 A | 3/2000 | Diab et al. |
| 6,036,718 A | 3/2000 | Ledford et al. |
| 6,040,578 A | 3/2000 | Malin et al. |
| 6,045,509 A | 4/2000 | Caro et al. |
| 6,045,527 A | 4/2000 | Appelbaum et al. |
| 6,057,758 A | 5/2000 | Dempsey et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,108,199 A | 8/2000 | Bonardi et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,175,752 B1 | 1/2001 | Say et al. |
| 6,183,417 B1 | 2/2001 | Gehab et al. |
| 6,184,521 B1 | 2/2001 | Coffin, IV et al. |
| 6,206,830 B1 | 3/2001 | Diab et al. |
| 6,221,012 B1 | 4/2001 | Maschke et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano et al. |

(56) References Cited

U.S. PATENT DOCUMENTS

| | | |
|---|---|---|
| 6,251,113 B1 | 6/2001 | Appelbaum |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,275,378 B1 | 8/2001 | Lee et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,304,767 B1 | 10/2001 | Soller et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,344,025 B1 | 2/2002 | Inagaki et al. |
| 6,349,228 B1 | 2/2002 | Kiani et al. |
| 6,352,504 B1 | 3/2002 | Ise |
| 6,354,235 B1 | 3/2002 | Davies |
| 6,360,114 B1 | 3/2002 | Diab et al. |
| 6,364,839 B1 | 4/2002 | Little et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,407,335 B1 | 6/2002 | Franklin-Lees |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,440,072 B1 | 8/2002 | Schuman et al. |
| 6,463,311 B1 | 10/2002 | Diab |
| 6,470,199 B1 | 10/2002 | Kopotic et al. |
| 6,470,893 B1 | 10/2002 | Boesen |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,516,289 B2 | 2/2003 | David et al. |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,544,173 B2 | 4/2003 | West et al. |
| 6,544,174 B2 | 4/2003 | West et al. |
| 6,570,592 B1 | 5/2003 | Sajdak et al. |
| 6,578,428 B1 | 6/2003 | Dromms et al. |
| 6,580,086 B1 | 6/2003 | Schulz et al. |
| 6,582,393 B2 | 6/2003 | Sage, Jr. |
| 6,584,336 B1 | 6/2003 | Ali et al. |
| 6,587,196 B1 | 7/2003 | Stippick et al. |
| 6,587,199 B1 | 7/2003 | Luu |
| 6,594,762 B1 | 7/2003 | Doub et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey et al. |
| 6,643,530 B2 | 11/2003 | Diab et al. |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Kiani et al. |
| 6,661,161 B1 | 12/2003 | Lanzo et al. |
| 6,663,570 B2 | 12/2003 | Mott et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,707,476 B1 | 3/2004 | Hochstedler |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,725,086 B2 | 4/2004 | Marinello |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,746,406 B2 | 6/2004 | Lia et al. |
| 6,749,566 B2 | 6/2004 | Russ |
| 6,750,463 B1 | 6/2004 | Riley |
| 6,760,607 B2 | 7/2004 | Al-Ali |
| 6,766,188 B2 | 7/2004 | Seller |
| 6,770,028 B1 | 8/2004 | Ali et al. |
| 6,771,994 B2 | 8/2004 | Kiani et al. |
| 6,773,396 B2 | 8/2004 | Flach et al. |
| 6,788,965 B2 | 9/2004 | Ruchti et al. |
| 6,790,178 B1 | 9/2004 | Mault et al. |
| 6,792,300 B1 | 9/2004 | Diab et al. |
| 6,796,186 B2 | 9/2004 | Lia et al. |
| 6,807,050 B1 | 10/2004 | Whitehorn et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,897,788 B2 | 5/2005 | Khair et al. |
| 6,898,452 B2 | 5/2005 | Al-Ali et al. |
| 6,907,237 B1 | 6/2005 | Dorenbosch et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,980,419 B2 | 12/2005 | Smith et al. |
| 6,985,764 B2 | 1/2006 | Mason et al. |
| 6,988,989 B2 | 1/2006 | Weiner et al. |
| 6,990,087 B2 | 1/2006 | Rao et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,004,907 B2 | 2/2006 | Banet et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |

(56) References Cited

U.S. PATENT DOCUMENTS

| | | |
|---|---|---|
| 7,039,449 B2 | 5/2006 | Al-Ali |
| 7,041,060 B2 | 5/2006 | Flaherty et al. |
| 7,044,918 B2 | 5/2006 | Diab |
| 7,044,930 B2 | 5/2006 | Stromberg |
| 7,059,769 B1 | 6/2006 | Potega |
| 7,061,428 B1 | 6/2006 | Amir et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,179,228 B2 | 2/2007 | Banet |
| 7,186,966 B2 | 3/2007 | Al-Ali |
| 7,188,621 B2 | 3/2007 | DeVries et al. |
| 7,190,261 B2 | 3/2007 | Al-Ali |
| 7,208,119 B1 | 4/2007 | Kurtock et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,238,159 B2 | 7/2007 | Banet et al. |
| 7,239,905 B2 | 7/2007 | Kiani-Azarbayjany et al. |
| 7,245,373 B2 | 7/2007 | Soller et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,261,697 B2 | 8/2007 | Berstein |
| 7,268,859 B2 | 9/2007 | Sage, Jr. et al. |
| 7,272,425 B2 | 9/2007 | Al-Ali |
| 7,273,454 B2 | 9/2007 | Raymond et al. |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,294,105 B1 | 11/2007 | Islam |
| 7,295,866 B2 | 11/2007 | Al-Ali |
| 7,312,709 B2 | 12/2007 | Kingston |
| 7,313,423 B2 | 12/2007 | Griffin et al. |
| 7,328,053 B1 | 2/2008 | Diab et al. |
| 7,332,784 B2 | 2/2008 | Mills et al. |
| 7,336,187 B2 | 2/2008 | Hubbard, Jr. et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,155 B2 | 4/2008 | Sage, Jr. et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,374,535 B2 | 5/2008 | Schoenberg et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,382,247 B2 | 6/2008 | Welch et al. |
| 7,383,070 B2 | 6/2008 | Diab et al. |
| 7,390,299 B2 | 6/2008 | Weiner et al. |
| 7,395,158 B2 | 7/2008 | Monfre et al. |
| 7,396,330 B2 | 7/2008 | Banet et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,439,856 B2 | 10/2008 | Weiner et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,481,772 B2 | 1/2009 | Banet |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,515,043 B2 | 4/2009 | Welch et al. |
| 7,515,044 B2 | 4/2009 | Welch et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,532,919 B2 | 5/2009 | Soyemi et al. |
| 7,549,961 B1 | 6/2009 | Hwang |
| 7,559,520 B2 | 7/2009 | Quijano et al. |
| 7,563,110 B2 | 7/2009 | Al-Ali et al. |
| 7,588,558 B2 | 9/2009 | Sage, Jr. et al. |
| 7,590,950 B2 | 9/2009 | Collins et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,612,999 B2 | 11/2009 | Clark et al. |
| 7,616,303 B2 | 11/2009 | Yang et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,658,716 B2 | 2/2010 | Banet et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,722,542 B2 | 5/2010 | Lia et al. |
| 7,729,733 B2 | 6/2010 | Al-Ali et al. |
| 7,734,320 B2 | 6/2010 | Al-Ali |
| 7,740,590 B2 | 6/2010 | Bernstein |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,515 S | 8/2010 | Chua et al. |
| D621,516 S | 8/2010 | Kiani et al. |
| 7,772,799 B2 | 8/2010 | Wu |
| 7,791,155 B2 | 9/2010 | Diab |
| 7,801,581 B2 | 9/2010 | Diab |
| 7,803,120 B2 | 9/2010 | Banet et al. |
| 7,806,830 B2 | 10/2010 | Bernstein |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,892 B2 | 2/2011 | Soyemi et al. |
| 7,884,314 B2 | 2/2011 | Hamada |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |

(56) References Cited

U.S. PATENT DOCUMENTS

| | | |
|---|---|---|
| 7,904,132 B2 | 3/2011 | Weber et al. |
| 7,907,945 B2 | 3/2011 | Deprun |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 7,993,275 B2 | 8/2011 | Banet et al. |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| 8,094,013 B1 | 1/2012 | Lee et al. |
| 8,107,397 B1 | 1/2012 | Bagchi et al. |
| RE43,169 E | 2/2012 | Parker |
| 8,118,620 B2 | 2/2012 | Al-Ali et al. |
| 8,130,105 B2 | 3/2012 | Al-Ali et al. |
| D659,836 S | 5/2012 | Bensch et al. |
| 8,180,440 B2 | 5/2012 | McCombie et al. |
| 8,182,429 B2 | 5/2012 | Mason |
| 8,182,443 B1 | 5/2012 | Kiani |
| 8,190,223 B2 | 5/2012 | Al-Ali et al. |
| 8,200,308 B2 | 6/2012 | Zhang et al. |
| 8,200,321 B2 | 6/2012 | McCombie et al. |
| 8,203,438 B2 | 6/2012 | Kiani et al. |
| 8,203,704 B2 | 6/2012 | Merritt et al. |
| 8,214,007 B2 | 7/2012 | Baker et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,239,010 B2 | 8/2012 | Banet et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,294,588 B2 | 10/2012 | Fisher et al. |
| 8,315,683 B2 | 11/2012 | Al-Ali et al. |
| 8,321,004 B2 | 11/2012 | Moon et al. |
| RE43,860 E | 12/2012 | Parker |
| 8,328,793 B2 | 12/2012 | Birkenbach et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,364,250 B2 | 1/2013 | Moon et al. |
| 8,374,665 B2 | 2/2013 | Lamego |
| D679,018 S | 3/2013 | Fullerton et al. |
| 8,388,353 B2 | 3/2013 | Kiani |
| 8,401,602 B2 | 3/2013 | Kiani |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,428,967 B2 | 4/2013 | Olsen et al. |
| 8,430,817 B1 | 4/2013 | Al-Ali et al. |
| 8,437,824 B2 | 5/2013 | Moon et al. |
| 8,437,825 B2 | 5/2013 | Dalvi et al. |
| 8,442,607 B2 | 5/2013 | Banet et al. |
| 8,449,469 B2 | 5/2013 | Banet et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,475,370 B2 | 7/2013 | McCombie et al. |
| 8,489,167 B2 | 7/2013 | Buxton et al. |
| 8,506,480 B2 | 8/2013 | Banet et al. |
| 8,509,867 B2 | 8/2013 | Workman et al. |
| 8,514,086 B2 | 8/2013 | Harper et al. |
| 8,515,509 B2 | 8/2013 | Bruinsma et al. |
| 8,523,781 B2 | 9/2013 | Al-Ali |
| 8,527,038 B2 | 9/2013 | Moon et al. |
| D692,145 S | 10/2013 | Al-Ali et al. |
| 8,545,417 B2 | 10/2013 | Banet et al. |
| 8,549,600 B2 | 10/2013 | Shedrinsky |
| 8,554,297 B2 | 10/2013 | Moon et al. |
| 8,565,847 B2 | 10/2013 | Buxton et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,574,161 B2 | 11/2013 | Banet et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,588,924 B2 | 11/2013 | Dion |
| 8,591,411 B2 | 11/2013 | Banet et al. |
| 8,594,776 B2 | 11/2013 | McCombie et al. |
| 8,597,287 B2 | 12/2013 | Benamou et al. |
| 8,602,997 B2 | 12/2013 | Banet et al. |
| 8,622,922 B2 | 1/2014 | Banet et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| 8,672,854 B2 | 3/2014 | McCombie et al. |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,727,977 B2 | 5/2014 | Banet et al. |
| 8,737,048 B2 | 5/2014 | Fidacaro et al. |
| 8,738,118 B2 | 5/2014 | Moon et al. |
| 8,740,792 B1 | 6/2014 | Kiani et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,753,274 B2 | 6/2014 | Ziv et al. |
| 8,755,535 B2 | 6/2014 | Telfort et al. |
| 8,755,872 B1 | 6/2014 | Marinow |
| 8,758,020 B2 | 6/2014 | Burdea et al. |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,792,950 B2 | 7/2014 | Larsen et al. |
| 8,801,613 B2 | 8/2014 | Al-Ali et al. |
| 8,808,188 B2 | 8/2014 | Banet et al. |
| 8,818,477 B2 | 8/2014 | Soller |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,873,035 B2 | 10/2014 | Yang et al. |
| 8,873,419 B2 | 10/2014 | Soomro |
| 8,882,666 B1 | 11/2014 | Goldberg et al. |
| 8,888,700 B2 | 11/2014 | Banet et al. |
| 8,897,847 B2 | 11/2014 | Al-Ali |
| 8,909,330 B2 | 12/2014 | McCombie et al. |
| 8,911,377 B2 | 12/2014 | Al-Ali |
| 8,951,248 B2 | 2/2015 | Messerly et al. |
| 8,956,292 B2 | 2/2015 | Wekell et al. |
| 8,956,293 B2 | 2/2015 | McCombie et al. |
| 8,956,294 B2 | 2/2015 | McCombie et al. |
| 8,979,765 B2 | 3/2015 | Banet et al. |
| 8,989,831 B2 | 3/2015 | Al-Ali et al. |
| 8,998,809 B2 | 4/2015 | Kiani |
| 9,055,928 B2 | 6/2015 | McCombie et al. |
| 9,057,689 B2 | 6/2015 | Soller |
| 9,066,666 B2 | 6/2015 | Kiani |
| 9,066,680 B1 | 6/2015 | Al-Ali et al. |

(56) References Cited

U.S. PATENT DOCUMENTS

| | | |
|---|---|---|
| 9,095,291 B2 | 8/2015 | Soller |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,125,578 B2 | 9/2015 | Grunwald |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,149,192 B2 | 10/2015 | Banet et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,700 B2 | 10/2015 | Banet et al. |
| 9,161,713 B2 | 10/2015 | Al-Ali et al. |
| 9,167,995 B2 | 10/2015 | Lamego et al. |
| 9,173,593 B2 | 11/2015 | Banet et al. |
| 9,173,594 B2 | 11/2015 | Banet et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| 9,211,072 B2 | 12/2015 | Kiani |
| 9,211,095 B1 | 12/2015 | Al-Ali |
| 9,215,986 B2 | 12/2015 | Banet et al. |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,915 B2 | 4/2016 | McCombie et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,209 B2 | 5/2016 | Banet et al. |
| 9,339,211 B2 | 5/2016 | Banet et al. |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,158 B2 | 6/2016 | Banet et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,380,952 B2 | 7/2016 | Banet et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,408,573 B2 | 8/2016 | Welch et al. |
| 9,414,784 B1 | 8/2016 | Berme et al. |
| 9,436,645 B2 | 9/2016 | Al-Ali et al. |
| 9,439,574 B2 | 9/2016 | McCombie et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,529,762 B2 | 12/2016 | Gisler et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,031 B1 | 7/2018 | Liu et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,383,520 B2 | 8/2019 | Wojitczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |

(56) References Cited

U.S. PATENT DOCUMENTS

| | | |
|---|---|---|
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Sherim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| 11,678,829 B2 | 6/2023 | Al-Ali et al. |
| 11,684,296 B2 | 6/2023 | Vo et al. |
| 11,692,934 B2 | 7/2023 | Normand et al. |
| 11,701,043 B2 | 7/2023 | Al-Ali et al. |
| 11,721,105 B2 | 8/2023 | Ranasinghe et al. |
| 2001/0011355 A1 | 8/2001 | Kawai |
| 2001/0028674 A1 | 10/2001 | Edlis et al. |
| 2001/0034477 A1 | 10/2001 | Mansfield et al. |
| 2001/0039199 A1 | 11/2001 | Shinzaki |
| 2001/0039483 A1 | 11/2001 | Brand et al. |
| 2001/0046862 A1 | 11/2001 | Coppinger et al. |
| 2001/0055978 A1 | 12/2001 | Herrod et al. |
| 2002/0010401 A1 | 1/2002 | Bushmakin et al. |
| 2002/0032386 A1 | 3/2002 | Sackner et al. |
| 2002/0044059 A1 | 4/2002 | Reeder et al. |
| 2002/0045836 A1 | 4/2002 | Alkawwas |
| 2002/0058864 A1 | 5/2002 | Mansfield et al. |
| 2002/0063690 A1 | 5/2002 | Chung et al. |
| 2002/0133080 A1 | 9/2002 | Apruzzese et al. |
| 2002/0165462 A1 | 11/2002 | Westbrook et al. |
| 2002/0177473 A1 | 11/2002 | Skinner et al. |
| 2002/0179470 A1 | 12/2002 | Lee |
| 2003/0013975 A1 | 1/2003 | Kiani |
| 2003/0018243 A1 | 1/2003 | Gerhardt et al. |
| 2003/0027326 A1 | 2/2003 | Ulmsten et al. |
| 2003/0083113 A1 | 5/2003 | Chua et al. |
| 2003/0144582 A1 | 7/2003 | Cohen et al. |
| 2003/0154108 A1 | 8/2003 | Fletcher-Haynes et al. |
| 2003/0156288 A1 | 8/2003 | Barnum et al. |
| 2003/0158466 A1 | 8/2003 | Lynn et al. |
| 2003/0181798 A1* | 9/2003 | Al-Ali ............... A61B 5/14552 600/324 |
| 2003/0212312 A1 | 11/2003 | Coffin, IV et al. |
| 2004/0009787 A1 | 1/2004 | Oh et al. |
| 2004/0029619 A1 | 2/2004 | Liang et al. |
| 2004/0073095 A1 | 4/2004 | Causey, III et al. |
| 2004/0090742 A1 | 5/2004 | Son et al. |
| 2004/0106163 A1 | 6/2004 | Workman, Jr. et al. |
| 2004/0139571 A1 | 7/2004 | Chang et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0249291 A1 | 12/2004 | Honda et al. |
| 2004/0249670 A1 | 12/2004 | Noguchi et al. |
| 2004/0267103 A1 | 12/2004 | Li et al. |
| 2005/0005710 A1 | 1/2005 | Sage, Jr. |
| 2005/0009926 A1 | 1/2005 | Kreye et al. |
| 2005/0038332 A1 | 2/2005 | Saidara et al. |
| 2005/0038680 A1 | 2/2005 | McMahon |
| 2005/0055276 A1 | 3/2005 | Kiani et al. |
| 2005/0113653 A1 | 5/2005 | Fox et al. |
| 2005/0148882 A1 | 7/2005 | Banet et al. |
| 2005/0171444 A1 | 8/2005 | Ono et al. |
| 2005/0188083 A1 | 8/2005 | Biondi et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228297 A1 | 10/2005 | Banet et al. |

(56) References Cited

U.S. PATENT DOCUMENTS

| | | |
|---|---|---|
| 2005/0228299 A1 | 10/2005 | Banet |
| 2005/0234317 A1 | 10/2005 | Kiani |
| 2005/0242946 A1 | 11/2005 | Hubbard et al. |
| 2005/0245831 A1 | 11/2005 | Banet |
| 2005/0261594 A1 | 11/2005 | Banet |
| 2005/0261598 A1 | 11/2005 | Banet et al. |
| 2005/0277819 A1 | 12/2005 | Kiani et al. |
| 2005/0277872 A1 | 12/2005 | Colby, Jr. et al. |
| 2006/0009697 A1 | 1/2006 | Banet et al. |
| 2006/0009698 A1 | 1/2006 | Banet et al. |
| 2006/0047214 A1 | 3/2006 | Fraden |
| 2006/0047215 A1 | 3/2006 | Barnes et al. |
| 2006/0052718 A1 | 3/2006 | Parnagian |
| 2006/0073719 A1 | 4/2006 | Kiani |
| 2006/0084878 A1 | 4/2006 | Banet et al. |
| 2006/0087606 A1 | 4/2006 | Munyon |
| 2006/0094936 A1 | 5/2006 | Russ |
| 2006/0122517 A1 | 6/2006 | Banet et al. |
| 2006/0154642 A1 | 7/2006 | Scannell, Jr. |
| 2006/0189871 A1 | 8/2006 | Al-Ali et al. |
| 2006/0200009 A1 | 9/2006 | Wekell et al. |
| 2006/0224413 A1 | 10/2006 | Kim et al. |
| 2006/0252418 A1 | 11/2006 | Quinn et al. |
| 2007/0000490 A1 | 1/2007 | DeVries et al. |
| 2007/0002533 A1 | 1/2007 | Kogan et al. |
| 2007/0027368 A1 | 2/2007 | Collins et al. |
| 2007/0030116 A1 | 2/2007 | Feher |
| 2007/0055116 A1 | 3/2007 | Clark et al. |
| 2007/0073116 A1 | 3/2007 | Kiani et al. |
| 2007/0079012 A1 | 4/2007 | Walker |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118853 A1 | 5/2007 | Kreitzer et al. |
| 2007/0140475 A1 | 6/2007 | Kurtock et al. |
| 2007/0142715 A1 | 6/2007 | Banet et al. |
| 2007/0156033 A1 | 7/2007 | Causey et al. |
| 2007/0157285 A1 | 7/2007 | Frank et al. |
| 2007/0163589 A1 | 7/2007 | DeVries et al. |
| 2007/0180140 A1 | 8/2007 | Welch et al. |
| 2007/0185390 A1 | 8/2007 | Perkins et al. |
| 2007/0185393 A1 | 8/2007 | Zhou et al. |
| 2007/0197881 A1 | 8/2007 | Wolf et al. |
| 2007/0244377 A1 | 10/2007 | Cozad et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg et al. |
| 2007/0276261 A1 | 11/2007 | Banet et al. |
| 2007/0276262 A1 | 11/2007 | Banet et al. |
| 2007/0276632 A1 | 11/2007 | Banet et al. |
| 2007/0282212 A1 | 12/2007 | Sierra et al. |
| 2007/0293906 A1 | 12/2007 | Cowan et al. |
| 2008/0020799 A1 | 1/2008 | Itamiya et al. |
| 2008/0051670 A1 | 2/2008 | Banet et al. |
| 2008/0053438 A1 | 3/2008 | DeVries et al. |
| 2008/0058614 A1 | 3/2008 | Banet et al. |
| 2008/0064965 A1 | 3/2008 | Jay et al. |
| 2008/0076972 A1 | 3/2008 | Dorogusker et al. |
| 2008/0077026 A1 | 3/2008 | Banet et al. |
| 2008/0082004 A1 | 4/2008 | Banet et al. |
| 2008/0090626 A1 | 4/2008 | Griffin et al. |
| 2008/0094228 A1 | 4/2008 | Welch et al. |
| 2008/0099366 A1 | 5/2008 | Niemiec et al. |
| 2008/0114220 A1 | 5/2008 | Banet et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0198822 A1 | 8/2008 | Magnusson et al. |
| 2008/0215627 A1 | 9/2008 | Higgins et al. |
| 2008/0221396 A1 | 9/2008 | Garces et al. |
| 2008/0221399 A1 | 9/2008 | Zhou et al. |
| 2008/0221418 A1 | 9/2008 | Al-Ali et al. |
| 2008/0221461 A1 | 9/2008 | Zhou et al. |
| 2008/0228045 A1 | 9/2008 | Gao et al. |
| 2008/0259551 A1 | 10/2008 | Gavenda et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0287751 A1 | 11/2008 | Stivoric et al. |
| 2008/0300020 A1 | 12/2008 | Nishizawa et al. |
| 2008/0312542 A1 | 12/2008 | Banet et al. |
| 2008/0319275 A1 | 12/2008 | Chiu et al. |
| 2008/0319327 A1 | 12/2008 | Banet et al. |
| 2008/0319354 A1 | 12/2008 | Bell et al. |
| 2009/0005651 A1 | 1/2009 | Ward et al. |
| 2009/0018409 A1* | 1/2009 | Banet ............... A61B 5/6826 600/301 |
| 2009/0018422 A1 | 1/2009 | Banet et al. |
| 2009/0018453 A1 | 1/2009 | Banet et al. |
| 2009/0036759 A1 | 2/2009 | Ault et al. |
| 2009/0043172 A1 | 2/2009 | Zagorchev et al. |
| 2009/0081951 A1 | 3/2009 | Erdmann et al. |
| 2009/0093687 A1 | 4/2009 | Telfort et al. |
| 2009/0095926 A1 | 4/2009 | MacNeish, III |
| 2009/0112072 A1 | 4/2009 | Banet et al. |
| 2009/0118628 A1 | 5/2009 | Zhou et al. |
| 2009/0147024 A1 | 6/2009 | Sadler |
| 2009/0154432 A1 | 6/2009 | Hassan et al. |
| 2009/0171170 A1 | 7/2009 | Li et al. |
| 2009/0221887 A1 | 9/2009 | Mannheimer et al. |
| 2009/0247984 A1 | 10/2009 | Lamego et al. |
| 2009/0275813 A1 | 11/2009 | Davis |
| 2009/0295328 A1 | 12/2009 | Griffin, Jr. |
| 2009/0309755 A1 | 12/2009 | Williamson |
| 2009/0322540 A1 | 12/2009 | Richardson et al. |
| 2009/0326386 A1 | 12/2009 | Sethi et al. |
| 2009/0326395 A1* | 12/2009 | Watson ............... A61B 5/021 600/500 |
| 2010/0004518 A1 | 1/2010 | Vo et al. |
| 2010/0030040 A1 | 2/2010 | Poeze et al. |
| 2010/0060747 A1 | 3/2010 | Woodman |
| 2010/0081895 A1 | 4/2010 | Zand |
| 2010/0099964 A1 | 4/2010 | O'Reilly et al. |
| 2010/0114254 A1 | 5/2010 | Kornet |
| 2010/0125188 A1 | 5/2010 | Schilling et al. |
| 2010/0130875 A1* | 5/2010 | Banet ............... A61B 5/6838 600/490 |
| 2010/0145146 A1 | 6/2010 | Melder |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168536 A1 | 7/2010 | Banet et al. |
| 2010/0168589 A1 | 7/2010 | Banet et al. |
| 2010/0173532 A1 | 7/2010 | Czyz et al. |
| 2010/0177100 A1 | 7/2010 | Carnes et al. |
| 2010/0182518 A1 | 7/2010 | Kirmse et al. |
| 2010/0234706 A1 | 9/2010 | Gilland |
| 2010/0234718 A1 | 9/2010 | Sampath et al. |
| 2010/0240945 A1 | 9/2010 | Bikko |
| 2010/0241115 A1 | 9/2010 | Benamou et al. |
| 2010/0249540 A1 | 9/2010 | Lisogurski |
| 2010/0250975 A1 | 9/2010 | Gill et al. |
| 2010/0270257 A1 | 10/2010 | Wachman et al. |
| 2010/0274099 A1 | 10/2010 | Telfort et al. |
| 2010/0280339 A1 | 11/2010 | Russ |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0298742 A1 | 11/2010 | Perlman et al. |
| 2010/0324384 A1 | 12/2010 | Moon et al. |
| 2010/0324385 A1 | 12/2010 | Moon et al. |
| 2010/0324386 A1 | 12/2010 | Moon et al. |

(56) References Cited

U.S. PATENT DOCUMENTS

| | | |
|---|---|---|
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331631 A1* | 12/2010 | MacLaughlin ...... A61B 5/6817 600/301 |
| 2011/0004489 A1 | 1/2011 | Schoenberg et al. |
| 2011/0015533 A1 | 1/2011 | Cox et al. |
| 2011/0023130 A1 | 1/2011 | Gudgel et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0066045 A1 | 3/2011 | Moon et al. |
| 2011/0077473 A1 | 3/2011 | Lisogurski |
| 2011/0077487 A1 | 3/2011 | Buxton et al. |
| 2011/0077488 A1 | 3/2011 | Buxton et al. |
| 2011/0078596 A1 | 3/2011 | Rawlins et al. |
| 2011/0082711 A1 | 4/2011 | Poeze et al. |
| 2011/0084850 A1 | 4/2011 | Jiang et al. |
| 2011/0087081 A1 | 4/2011 | Kiani et al. |
| 2011/0087756 A1 | 4/2011 | Biondi |
| 2011/0105956 A1 | 5/2011 | Hirth |
| 2011/0118561 A1 | 5/2011 | Tari et al. |
| 2011/0118616 A1 | 5/2011 | Vajdic et al. |
| 2011/0137297 A1 | 6/2011 | Kiani et al. |
| 2011/0148622 A1 | 6/2011 | Judy et al. |
| 2011/0149871 A1 | 6/2011 | Liu et al. |
| 2011/0152629 A1 | 6/2011 | Eaton et al. |
| 2011/0172498 A1 | 7/2011 | Olsen et al. |
| 2011/0193704 A1 | 8/2011 | Harper et al. |
| 2011/0208015 A1 | 8/2011 | Welch et al. |
| 2011/0212746 A1 | 9/2011 | Sarkar et al. |
| 2011/0213274 A1* | 9/2011 | Telfort ................. A61B 5/7214 600/586 |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon et al. |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0227739 A1 | 9/2011 | Gilham et al. |
| 2011/0230733 A1 | 9/2011 | Al-Ali |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |
| 2011/0288421 A1 | 11/2011 | Banet et al. |
| 2011/0307274 A1 | 12/2011 | Thompson et al. |
| 2012/0029304 A1 | 2/2012 | Medina et al. |
| 2012/0095778 A1 | 4/2012 | Gross et al. |
| 2012/0102455 A1 | 4/2012 | Ambat et al. |
| 2012/0108917 A1 | 5/2012 | Libbus et al. |
| 2012/0108983 A1 | 5/2012 | Banet et al. |
| 2012/0123231 A1 | 5/2012 | O'Reilly |
| 2012/0127103 A1 | 5/2012 | Qualey et al. |
| 2012/0157806 A1 | 6/2012 | Steiger et al. |
| 2012/0165629 A1 | 6/2012 | Merritt et al. |
| 2012/0179011 A1 | 7/2012 | Moon et al. |
| 2012/0184120 A1 | 7/2012 | Basta et al. |
| 2012/0190949 A1 | 7/2012 | McCombie et al. |
| 2012/0198341 A1 | 8/2012 | Pekarske et al. |
| 2012/0209084 A1 | 8/2012 | Olsen et al. |
| 2012/0221634 A1 | 8/2012 | Treu et al. |
| 2012/0224694 A1 | 9/2012 | Lu et al. |
| 2012/0226117 A1 | 9/2012 | Lamego et al. |
| 2012/0275392 A1 | 11/2012 | Haddad |
| 2012/0283524 A1 | 11/2012 | Kiani et al. |
| 2012/0303476 A1 | 11/2012 | Krzyzanowski et al. |
| 2013/0023775 A1 | 1/2013 | Lamego et al. |
| 2013/0041591 A1 | 2/2013 | Lamego |
| 2013/0046197 A1 | 2/2013 | Dlugos, Jr. et al. |
| 2013/0060147 A1 | 3/2013 | Welch et al. |
| 2013/0092805 A1 | 4/2013 | Funk et al. |
| 2013/0096405 A1 | 4/2013 | Garfio |
| 2013/0109929 A1 | 5/2013 | Menzel |
| 2013/0109937 A1 | 5/2013 | Banet et al. |
| 2013/0116515 A1 | 5/2013 | Banet et al. |
| 2013/0123616 A1 | 5/2013 | Merritt et al. |
| 2013/0178718 A1 | 7/2013 | Tran et al. |
| 2013/0191513 A1 | 7/2013 | Kamen et al. |
| 2013/0197364 A1 | 8/2013 | Han |
| 2013/0267793 A1 | 10/2013 | Meador et al. |
| 2013/0279109 A1 | 10/2013 | Lindblad et al. |
| 2013/0286853 A1 | 10/2013 | Shi et al. |
| 2013/0296672 A1 | 11/2013 | O'Neil et al. |
| 2013/0324804 A1 | 12/2013 | McKeown et al. |
| 2013/0331054 A1 | 12/2013 | Kodali |
| 2013/0332011 A1 | 12/2013 | Ziarno |
| 2013/0344872 A1 | 12/2013 | Nukala et al. |
| 2013/0345921 A1 | 12/2013 | Al-Ali et al. |
| 2014/0025010 A1 | 1/2014 | Stroup et al. |
| 2014/0031637 A1 | 1/2014 | Fidacaro et al. |
| 2014/0081099 A1 | 3/2014 | Banet et al. |
| 2014/0088385 A1 | 3/2014 | Moon et al. |
| 2014/0142445 A1 | 5/2014 | Banet et al. |
| 2014/0152673 A1 | 6/2014 | Lynn et al. |
| 2014/0163393 A1 | 6/2014 | McCombie et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0188516 A1 | 7/2014 | Kamen |
| 2014/0200415 A1 | 7/2014 | McCombie et al. |
| 2014/0235964 A1 | 8/2014 | Banet et al. |
| 2014/0249431 A1 | 9/2014 | Banet et al. |
| 2014/0249432 A1 | 9/2014 | Banet et al. |
| 2014/0249433 A1 | 9/2014 | Banet et al. |
| 2014/0249434 A1 | 9/2014 | Banet et al. |
| 2014/0249435 A1 | 9/2014 | Banet et al. |
| 2014/0249440 A1 | 9/2014 | Banet et al. |
| 2014/0249441 A1 | 9/2014 | Banet et al. |
| 2014/0249442 A1 | 9/2014 | Banet et al. |
| 2014/0257056 A1 | 9/2014 | Moon et al. |
| 2014/0275871 A1 | 9/2014 | Lamego et al. |
| 2014/0275872 A1 | 9/2014 | Merritt et al. |
| 2014/0276145 A1 | 9/2014 | Banet et al. |
| 2014/0276175 A1 | 9/2014 | Banet et al. |
| 2014/0301893 A1 | 10/2014 | Stroup et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0006089 A1 | 1/2015 | Pagels |
| 2015/0007075 A1 | 1/2015 | Choi et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2015/0164437 A1 | 6/2015 | McCombie et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0264506 A1 | 9/2015 | Balabanis et al. |
| 2015/0272514 A1 | 10/2015 | Kiani et al. |
| 2015/0282717 A1 | 10/2015 | McCombie et al. |
| 2015/0351697 A1 | 12/2015 | Weber et al. |
| 2015/0351704 A1 | 12/2015 | Kiani et al. |
| 2015/0358314 A1 | 12/2015 | Glik et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |

(56) References Cited

U.S. PATENT DOCUMENTS

| | | |
|---|---|---|
| 2016/0007930 A1 | 1/2016 | Weber et al. |
| 2016/0022224 A1 | 1/2016 | Banet et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0045163 A1 | 2/2016 | Weisner et al. |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143546 A1 | 5/2016 | McCombie et al. |
| 2016/0143548 A1 | 5/2016 | Al-Ali |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0216117 A9 | 7/2016 | Bandyopadhyay et al. |
| 2016/0246781 A1 | 8/2016 | Cabot |
| 2016/0270717 A1 | 9/2016 | Luna et al. |
| 2016/0271445 A1 | 9/2016 | Kolloff |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0216370 A1 | 8/2018 | Ishiguro et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2019/0015023 A1 | 1/2019 | Monfre |
| 2019/0053286 A1 | 2/2019 | Cho et al. |
| 2019/0090760 A1 | 3/2019 | Kinast et al. |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |

FOREIGN PATENT DOCUMENTS

| | | |
|---|---|---|
| EP | 2 144 181 | 1/2010 |
| EP | 2 335 569 | 6/2011 |
| JP | 02-050694 | 2/1990 |
| JP | 08-275926 | 10/1996 |
| JP | 09-187428 | 7/1997 |
| JP | 10-336064 | 12/1998 |
| JP | 2000-312668 | 11/2000 |
| JP | 2002-513602 | 5/2002 |
| JP | 2002-165764 | 6/2002 |
| JP | 2002-172096 | 6/2002 |
| JP | 2002-233512 | 8/2002 |
| JP | 2002-535026 | 10/2002 |
| JP | 2002-542493 | 12/2002 |
| JP | 2004-513732 | 5/2004 |
| JP | 2004-321603 | 11/2004 |
| JP | 2005-038417 | 2/2005 |
| JP | 2005-065721 | 3/2005 |

(56) References Cited

FOREIGN PATENT DOCUMENTS

| | | |
|---|---|---|
| JP | 2005-199064 | 7/2005 |
| JP | 2005-218036 | 8/2005 |
| JP | 2005-523755 | 8/2005 |
| JP | 2005-295375 | 10/2005 |
| JP | 2005-532849 | 11/2005 |
| JP | 2007-021213 | 2/2007 |
| JP | 2007-095365 | 4/2007 |
| JP | 2007-174051 | 7/2007 |
| JP | 2008-080136 | 4/2008 |
| JP | 2008-519635 | 6/2008 |
| JP | 2008-541045 | 11/2008 |
| JP | 2009-017959 | 1/2009 |
| JP | 2009-207836 | 9/2009 |
| JP | 2009-536868 | 10/2009 |
| JP | 2010-500051 | 1/2010 |
| JP | 2010-503134 | 1/2010 |
| JP | 2010-093543 | 4/2010 |
| JP | 2010-524510 | 7/2010 |
| JP | 2011-519607 | 7/2011 |
| JP | 2011-519684 | 7/2011 |
| JP | 2011-152261 | 8/2011 |
| JP | 2012-519547 | 8/2012 |
| JP | 2012-532363 | 12/2012 |
| JP | 2013-507228 | 3/2013 |
| KR | 2008-0091089 | 10/2008 |
| WO | WO 2007/143626 | 12/2007 |
| WO | WO 2009/134724 | 11/2009 |
| WO | WO 2010/054409 | 5/2010 |
| WO | WO 2011/001302 | 1/2011 |
| WO | WO 2011/002904 | 1/2011 |
| WO | WO 2011/021948 | 2/2011 |
| WO | WO 2011/025549 | 3/2011 |
| WO | WO 2011/041017 | 4/2011 |
| WO | WO 2013/056160 | 4/2013 |
| WO | WO 2013/119982 | 8/2013 |
| WO | WO 2015/054665 | 4/2015 |

OTHER PUBLICATIONS

Liu, Chun-Hung, "A Source Coding and Modulation Method for Power Saving and Interference Reduction in DS-CDMA Sensor Network Systems", Proceedings of the American Control Conference Anchorage, AK May 8-10, 2002, pp. 3003-3008.

International Search Report & Written Opinion in PCT Application No. PCT/US2013/025384, dated Aug. 6, 2013.

International Preliminary Report on Patentability & Written Opinion in PCT Application No. PCT/US2013/025384, dated Aug. 21, 2014.

International Search Report & Written Opinion in PCT Application No. PCT/US2012/060109, dated Jun. 5, 2013.

International Preliminary Reporton Patentability in PCT Application No. PCT/US2012/060109, dated Apr. 24, 2014.

International Search Report & Written Opinion in PCT Application No. PCT/US2014/060177, dated Dec. 19, 2014.

International Preliminary Report on Patentability & Written Opinion in PCT Application No. PCT/US2014/060177, dated Apr. 21, 2016.

Hudson, T.L., "Maximizing a Transport Platform Through Computer Technology", Computers, Informatics, Nursing: Mar.-Apr. 2003, vol. 21, No. 2, pp. 72-79.

\* cited by examiner

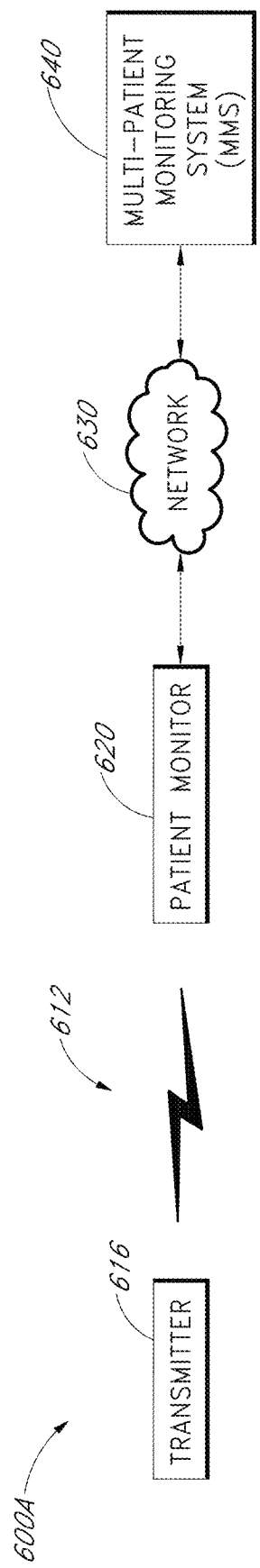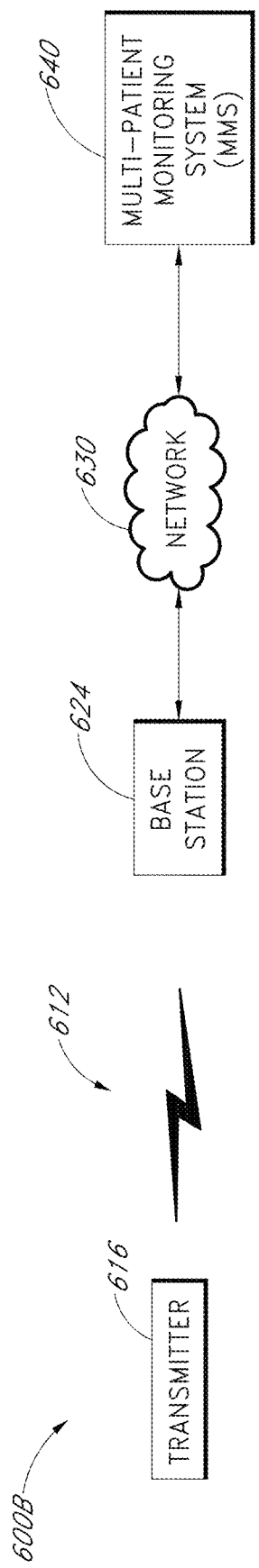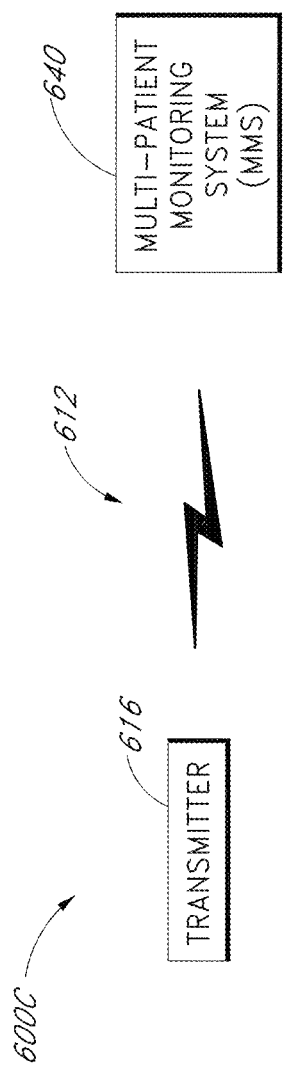
FIG. 6A
FIG. 6B
FIG. 6C

WIRELESS PATIENT MONITORING SYSTEM

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters such as blood oxygen saturation level, respiratory rate, and the like. Clinicians, including doctors, nurses, and other medical personnel, use the physiological parameters obtained from patient monitors to diagnose illnesses and to prescribe treatments. Clinicians also use the physiological parameters to monitor patients during various clinical situations to determine whether to increase the level of medical care given to patients.

Blood pressure is one example of a physiological parameter that can be monitored. Many devices allow blood pressure to be measured by sphygmomanometer systems that utilize an inflatable cuff applied to a person's arm. The cuff is inflated to a pressure level high enough to occlude a major artery. When air is slowly released from the cuff, blood pressure can be estimated by detecting "Korotkoff" sounds using a stethoscope or other detection means placed over the artery.

SUMMARY

In certain embodiments, a device for obtaining physiological information of a medical patient can include a blood pressure device that can be coupled to a medical patient and a wireless transceiver electrically coupled with the blood pressure device. The wireless transceiver can wirelessly transmit blood pressure data received by the blood pressure device and physiological data received from one or more physiological sensors coupled to the blood pressure device. To further increase patient mobility, in some embodiments, a single cable is also provided for connecting multiple different types of sensors together.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIGS. 6A through 6C illustrate additional embodiments of patient monitoring systems.

DETAILED DESCRIPTION

In clinical settings, medical sensors are often attached to patients to monitor physiological parameters of the patients. Some examples of medical sensors include blood oxygen sensors, blood pressure sensors, and acoustic respiratory sensors. Typically, each sensor attached to a patient is connected to a bedside monitoring device with a cable. The more cables that couple the patient to the bedside monitoring device, the more the patient's freedom of movement can be restricted. In addition, cables pose a tripping hazard to health care workers and make it difficult to perform rapid transport to therapeutic areas such as the operating room when emergency situations arise.

This disclosure describes embodiments of wireless patient monitoring systems that include a wireless device coupled to a patient and to one or more sensors. In one embodiment, the wireless device transmits sensor data obtained from the sensors to a patient monitor. By transmitting the sensor data wirelessly, these patient monitoring systems can advantageously replace some or all cables that connect patients to bedside monitoring devices. To further increase patient mobility and comfort, in some embodiments, a single cable connection system is also provided for connecting multiple different types of sensors together.

These patient monitoring systems are primarily described in the context of an example blood pressure cuff that includes a wireless transceiver. The blood pressure cuff and/or wireless transceiver can also be coupled to additional sensors, such as optical sensors, acoustic sensors, and/or electrocardiograph sensors. The wireless transceiver can transmit blood pressure data and sensor data from the other sensors to a wireless receiver, which can be a patient monitor. These and other features described herein can be applied to a variety of sensor configurations, including configurations that do not include a blood pressure cuff.

Figure 1A:
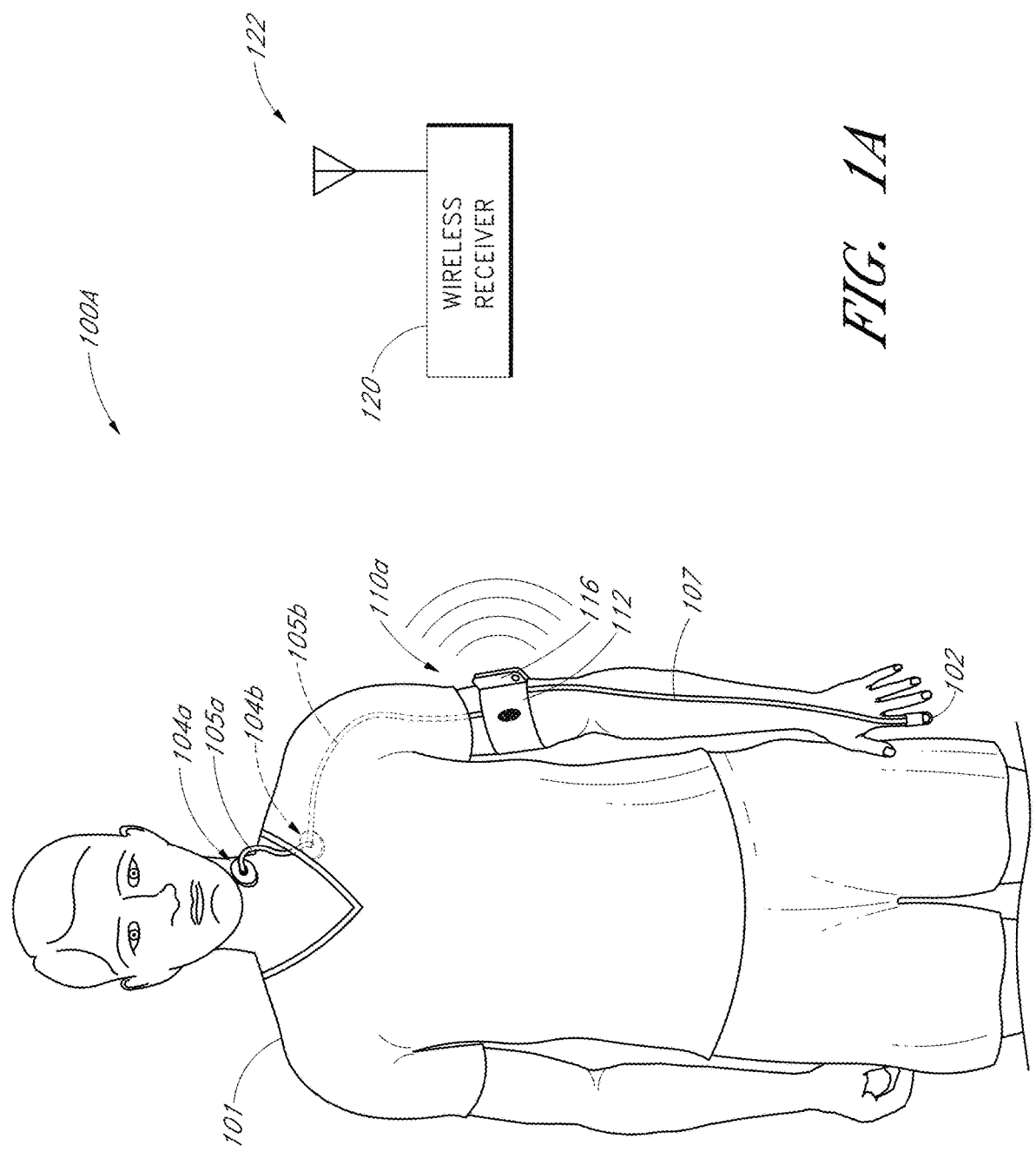
FIGS. 1A and 1B illustrate embodiments of wireless patient monitoring systems.
Figure 1B:
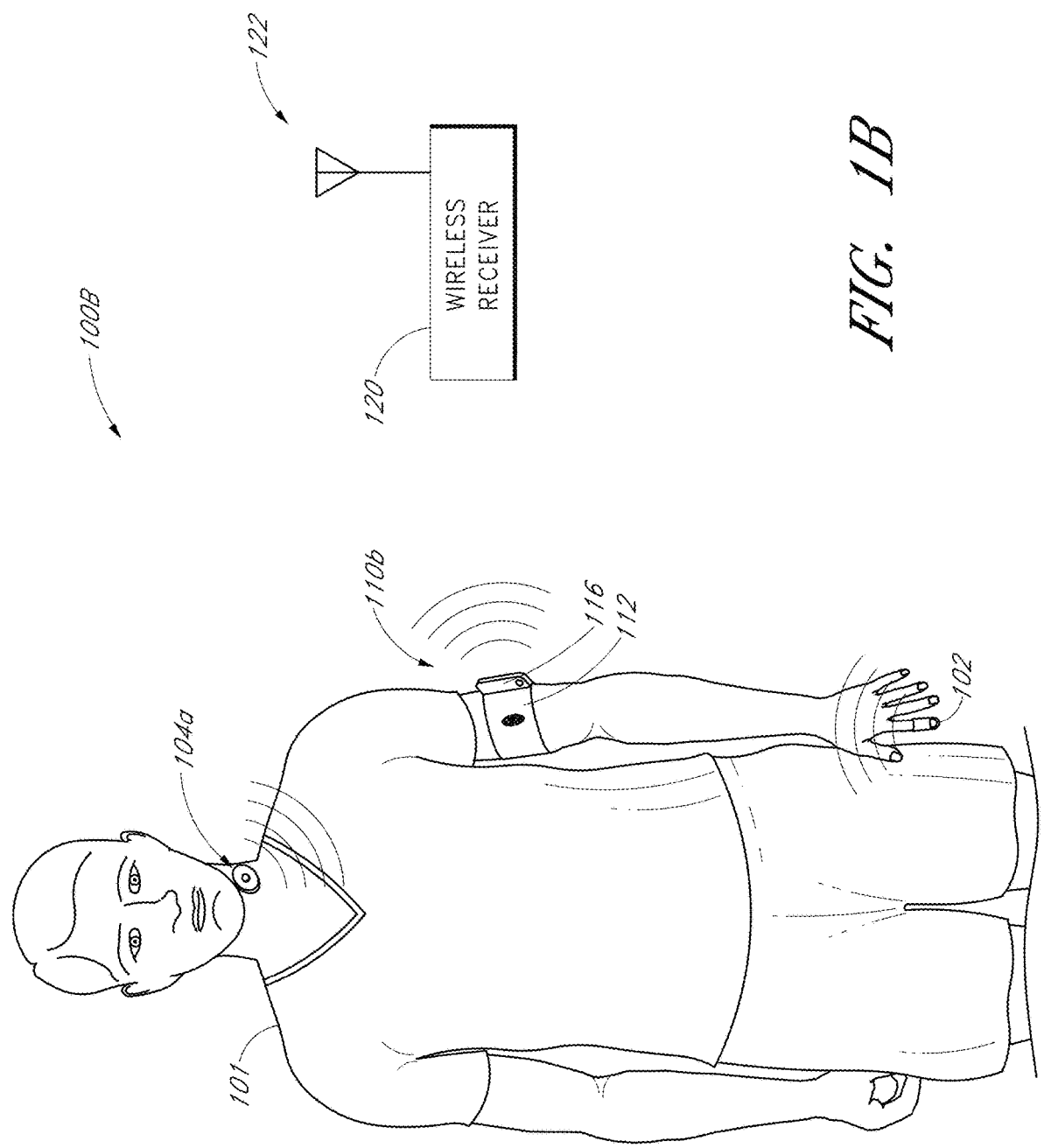

FIGS. 1A and 1B illustrate embodiments of wireless patient monitoring systems 100A, 100B, respectively. In the wireless patient monitoring systems 100 shown, a blood pressure device 110 is connected to a patient 101. The blood pressure device 110 includes a wireless transceiver 116, which can transmit sensor data obtained from the patient 101 to a wireless transreceiver 120. Thus, the patient 101 is advantageously not physically coupled to a bedside monitor in the depicted embodiment and can therefore have greater freedom of movement.

Referring to FIG. 1A, the blood pressure device 110*a* includes an inflatable cuff 112, which can be an oscillometric cuff that is actuated electronically (e.g., via intelligent cuff inflation and/or based on a time interval) to obtain blood pressure information. The cuff 112 is coupled to a wireless transceiver 116. The blood pressure device 110*a* is also coupled to a fingertip optical sensor 102 via a cable 107. The optical sensor 102 can include one or more emitters and detectors for obtaining physiological information indicative of one or more blood parameters of the patient 101. These parameters can include various blood analytes such as oxygen, carbon monoxide, methemoglobin, total hemoglobin, glucose, proteins, glucose, lipids, a percentage thereof (e.g., concentration or saturation), and the like. The optical sensor 102 can also be used to obtain a photoplethysmograph, a measure of plethysmograph variability, a measure of blood perfusion, and the like.

Additionally, the blood pressure device 110a is coupled to an acoustic sensor 104a via a cable 105. The cable 105 connecting the acoustic sensor 104a to the blood pressure device 110 includes two portions, namely a cable 105a and a cable 105b. The cable 105a connects the acoustic sensor 104a to an anchor 104b, which is coupled to the blood pressure device 110a via the cable 105b. The anchor 104b can be adhered to the patient's skin to reduce noise due to accidental tugging of the acoustic sensor 104a.

The acoustic sensor 104a can be a piezoelectric sensor or the like that obtains physiological information reflective of one or more respiratory parameters of the patient 101. These parameters can include, for example, respiratory rate, inspiratory time, expiratory time, inspiration-to-expiration ratio, inspiratory flow, expiratory flow, tidal volume, minute volume, apnea duration, breath sounds, rales, rhonchi, stridor, and changes in breath sounds such as decreased volume or change in airflow. In addition, in some cases the respiratory sensor 104a, or another lead of the respiratory sensor 104a (not shown), can measure other physiological sounds such as heart rate (e.g., to help with probe-off detection), heart sounds (e.g., S1, S2, S3, S4, and murmurs), and changes in heart sounds such as normal to murmur or split heart sounds indicating fluid overload. In some implementations, a second acoustic respiratory sensor can be provided over the patient's 101 chest for additional heart sound detection. In one embodiment, the acoustic sensor 104 can include any of the features described in U.S. Patent Application No. 61/141,584, filed Dec. 30, 2008, titled "Acoustic Sensor Assembly," the disclosure of which is hereby incorporated by reference in its entirety.

The acoustic sensor 104 can also be used to generate an exciter waveform that can be detected by the optical sensor 102 at the fingertip, by an optical sensor attached to an ear of the patient (see FIGS. 2A, 3), by an ECG sensor (see FIG. 2C), or by another acoustic sensor (not shown). The velocity of the exciter waveform can be calculated by a processor (such as a processor in the wireless transceiver 120, described below). From this velocity, the processor can derive a blood pressure measurement or blood pressure estimate. The processor can output the blood pressure measurement for display. The processor can also use the blood pressure measurement to determine whether to trigger the blood pressure cuff 112.

In another embodiment, the acoustic sensor 104 placed on the upper chest can be advantageously combined with an ECG electrode (such as in structure 208 of FIG. 2B), thereby providing dual benefit of two signals generated from a single mechanical assembly. The timing relationship from fidicial markers from the ECG signal, related cardiac acoustic signal and the resulting peripheral pulse from the finger pulse oximeters produces a transit time that correlates to the cardiovascular performance such as blood pressure, vascular tone, vascular volume and cardiac mechanical function. Pulse wave transit time or PWTT in currently available systems depends on ECG as the sole reference point, but such systems may not be able to isolate the transit time variables associated to cardiac functions, such as the pre-ejection period (PEP). In certain embodiments, the addition of the cardiac acoustical signal allows isolation of the cardiac functions and provides additional cardiac performance metrics. Timing calculations can be performed by the processor in the wireless transceiver 120 or a in distributed processor found in an on-body structure (e.g., such as any of the devices herein or below: 112, 210, 230, 402, 806).

In certain embodiments, the wireless patient monitoring system 100 uses some or all of the velocity-based blood pressure measurement techniques described in U.S. Pat. No. 5,590,649, filed Apr. 15, 1994, titled "Apparatus and Method for Measuring an Induced Perturbation to Determine Blood Pressure," or in U.S. Pat. No. 5,785,659, filed Jan. 17, 1996, titled "Automatically Activated Blood Pressure Measurement Device," the disclosures of which are hereby incorporated by reference in their entirety. An example display related to such blood pressure calculations is described below with respect to FIG. 7.

The wireless transceiver 116 can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like. The wireless transceiver 116 can perform solely telemetry functions, such as measuring and reporting information about the patient 101. Alternatively, the wireless transceiver 116 can be a transceiver that also receives data and/or instructions, as will be described in further detail below.

The wireless receiver 120 receives information from and/or sends information to the wireless transceiver via an antenna (not shown). In certain embodiments, the wireless receiver 120 is a patient monitor. As such, the wireless receiver 120 can include one or more processors that process sensor signals received from the wireless transceiver 116 corresponding to the sensors 102a, 102b, 104, and/or 106 in order to derive any of the physiological parameters described above. The wireless transceiver 120 can also display any of these parameters, including trends, waveforms, related alarms, and the like. The wireless receiver 120 can further include a computer-readable storage medium, such as a physical storage device, for storing the physiological data. The wireless transceiver 120 can also include a network interface for communicating the physiological data to one or more hosts over a network, such as to a nurse's station computer in a hospital network.

Moreover, in certain embodiments, the wireless transceiver 116 can send raw data for processing to a central nurse's station computer, to a clinician device, and/or to a bedside device (e.g., the receiver 116). The wireless transceiver 116 can also send raw data to a central nurse's station computer, clinician device, and/or to a bedside device for calculation, which retransmits calculated measurements back to the blood pressure device 110 (or to the bedside device). The wireless transceiver 116 can also calculate measurements from the raw data and send the measurements to a central nurse's station computer, to a pager or other clinician device, or to a bedside device (e.g., the receiver 116). Many other configurations of data transmission are possible.

In addition to deriving any of the parameters mentioned above from the data obtained from the sensors 102a, 102b, 104, and/or 106, the wireless transceiver 120 can also determine various measures of data confidence, such as the data confidence indicators described in U.S. Pat. No. 7,024,233 entitled "Pulse oximetry data confidence indicator," the disclosure of which is hereby incorporated by reference in its entirety. The wireless transceiver 120 can also determine a perfusion index, such as the perfusion index described in U.S. Pat. No. 7,292,883 entitled "Physiological assessment system," the disclosure of which is hereby incorporated by reference in its entirety. Moreover, the wireless transceiver 120 can determine a plethysmograph variability index (PVI), such as the PVI described in U.S. Publication No. 2008/0188760 entitled "Plethysmograph variability processor," the disclosure of which is hereby incorporated by reference in its entirety.

In addition, the wireless transceiver 120 can send data and instructions to the wireless transceiver 116 in some embodiments. For instance, the wireless transceiver 120 can intelligently determine when to inflate the cuff 112 and can send inflation signals to the transceiver 116. Similarly, the wireless transceiver 120 can remotely control any other sensors that can be attached to the transceiver 116 or the cuff 112. The transceiver 120 can send software or firmware updates to the transceiver 116. Moreover, the transceiver 120 (or the transceiver 116) can adjust the amount of signal data transmitted by the transceiver 116 based at least in part on the acuity of the patient, using, for example, any of the techniques described in U.S. Patent Publication No. 2009/0119330, filed Jan. 7, 2009, titled "Systems and Methods for Storing, Analyzing, and Retrieving Medical Data," the disclosure of which is hereby incorporated by reference in its entirety.

In alternative embodiments, the wireless transceiver 116 can perform some or all of the patient monitor functions described above, instead of or in addition to the monitoring functions described above with respect to the wireless transceiver 120. In some cases, the wireless transceiver 116 might also include a display that outputs data reflecting any of the parameters described above (see, e.g., FIG. 5). Thus, the wireless transceiver 116 can either send raw signal data to be processed by the wireless transceiver 120, can send processed signal data to be displayed and/or passed on by the wireless transceiver 120, or can perform some combination of the above. Moreover, in some implementations, the wireless transceiver 116 can perform at least some front-end processing of the data, such as bandpass filtering, analog-to-digital conversion, and/or signal conditioning, prior to sending the data to the transceiver 120. An alternative embodiment may include at least some front end processing embedded in any of the sensors described herein (such as sensors 102, 104, 204, 202, 208, 412, 804, 840, 808) or cable hub 806 (see FIG. 8).

In certain embodiments, the cuff 112 is a reusable, disposable, or resposable device. Similarly, any of the sensors 102, 104*a* or cables 105, 107 can be disposable or resposable. Resposable devices can include devices that are partially disposable and partially reusable. Thus, for example, the acoustic sensor 104*a* can include reusable electronics but a disposable contact surface (such as an adhesive) where the sensor 104*a* comes into contact with the patient's skin. Generally, any of the sensors, cuffs, and cables described herein can be reusable, disposable, or resposable.

The cuff 112 can also can have its own power (e.g., via batteries) either as extra power or as a sole source of power for the transceiver 116. The batteries can be disposable or reusable. In some embodiments, the cuff 112 can include one or more photovoltaic solar cells or other power sources. Likewise, batteries, solar sources, or other power sources can be provided for either of the sensors 102, 104*a*.

Referring to FIG. 1B, another embodiment of the system 100B is shown. In the system 100B, the blood pressure device 110*b* can communicate wirelessly with the acoustic sensor 104*a* and with the optical sensor 102. For instance, wireless transceivers (not shown) can be provided in one or both of the sensors 102, 104*a*, using any of the wireless technologies described above. The wireless transceivers can transmit data, raw signals, processed signals, conditioned signals, or the like to the blood pressure device 110*b*. The blood pressure device 110*b* can transmit these signals on to the wireless transceiver 120. In addition, in some embodiments, the blood pressure device 110*b* can also process the signals received from the sensors 102, 104*a* prior to transmitting the signals to the wireless transceiver 120. The sensors 102, 104*a* can also transmit data, raw signals, processed signals, conditioned signals, or the like directly to the wireless transceiver 120 or patient monitor. In one embodiment, the system 100B shown can be considered to be a body LAN, piconet, or other individual network.

Figure 2A:
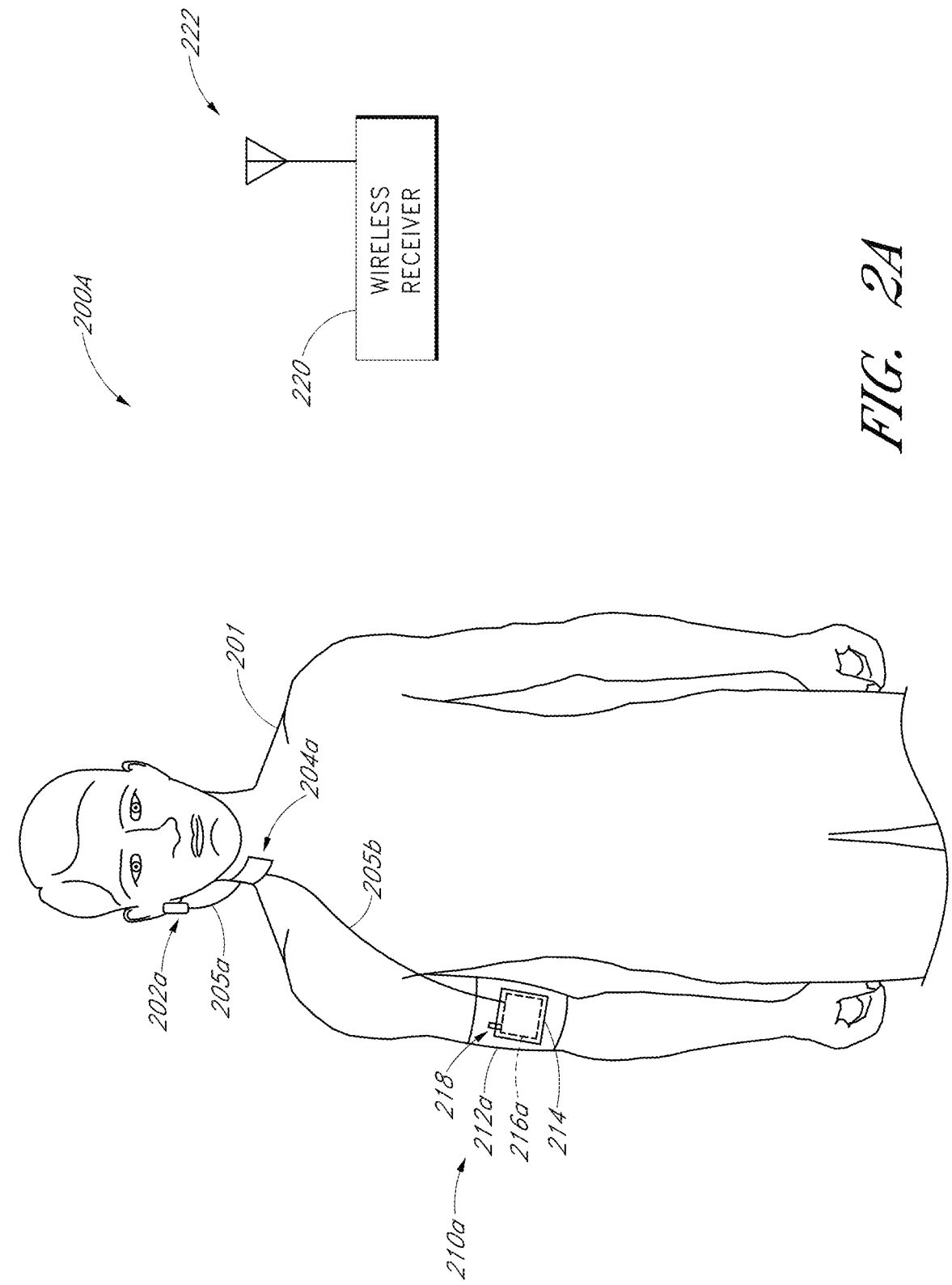
FIGS. 2A and 2B illustrate embodiments of wireless patient monitoring systems having a single cable connection system.
Figure 2B:
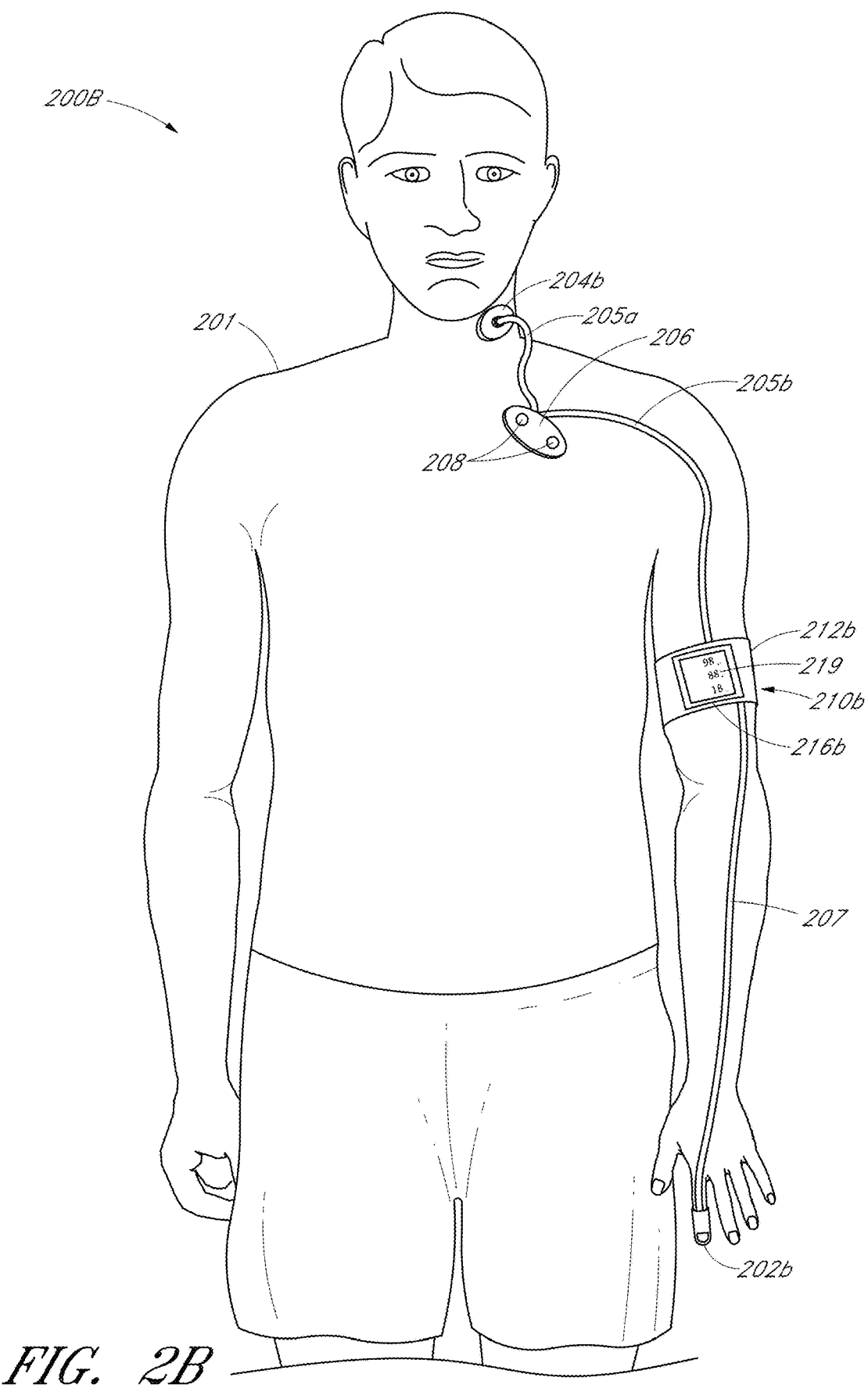

FIGS. 2A and 2B illustrate additional embodiments of patient monitoring systems 200A and 200B, respectively. In particular, FIG. 2A illustrates a wireless patient monitoring system 200A, while FIG. 2B illustrates a standalone patient monitoring system 200B.

Referring specifically to FIG. 2A, a blood pressure device 210*a* is connected to a patient 201. The blood pressure device 210*a* includes a wireless transceiver 216*a*, which can transmit sensor data obtained from the patient 201 to a wireless receiver at 220 via antenna 218. In the depicted embodiment, the blood pressure device 210*a* includes an inflatable cuff 212*a*, which can include any of the features of the cuff 112 described above. Additionally, the cuff 212*a* includes a pocket 214, which holds the wireless transceiver 216*a* (shown by dashed lines). The wireless transceiver 216*a* can be electrically connected to the cuff 212*a* via a connector (see, e.g., FIG. 5) in some embodiments. As will be described elsewhere herein, the form of attachment of the wireless transceiver 216*a* to the cuff 212*a* is not restricted to a pocket connection mechanism and can vary in other implementations.

The wireless transceiver 216*a* is also coupled to various sensors in FIG. 2A, including an acoustic sensor 204*a* and an optical ear sensor 202*a*. The acoustic sensor 204*a* can have any of the features of the acoustic sensor 104 described above. The ear clip sensor 202*a* can be an optical sensor that obtains physiological information regarding one or more blood parameters of the patient 201. These parameters can include any of the blood-related parameters described above with respect to the optical sensor 102. In one embodiment, the ear clip sensor 202*a* is an LNOP TC-I ear reusable sensor available from Masimo® Corporation of Irvine, Calif. In other embodiments, the ear clip sensor 202*a* is a concha ear sensor (see FIGS. 4A and 4B).

Advantageously, in the depicted embodiment, the sensors 202*a*, 204*a* are coupled to the wireless transceiver 216*a* via a single cable 205. The cable 205 is shown having two sections, a cable 205*a* and a cable 205*b*. For example, the wireless transceiver 216*a* is coupled to an acoustic sensor 204*a* via the cable 205*b*. In turn, the acoustic sensor 204*a* is coupled to the optical ear sensor 202*a* via the cable 205*a*. Advantageously, because the sensors 202*a*, 204 are attached to the wireless transceiver 216 in the cuff 212 in the depicted embodiment, the cable 205 is relatively short and can thereby increase the patient's 201 freedom of movement. Moreover, because a single cable 205 is used to connect both sensors 202*a*, 204*a*, the patient's mobility and comfort can be further enhanced.

In some embodiments, the cable 205 is a shared cable 205 that is shared by the optical ear sensor 202*a* and the acoustic sensor 204*a*. The shared cable 205 can share power and ground lines for each of the sensors 202a, 204a. Signal lines in the cable 205 can convey signals from the sensors 202a, 204a to the wireless transceiver 216 and/or instructions from the wireless transceiver 216 to the sensors 202a, 204a. The signal lines can be separate within the cable 205 for the different sensors 202a, 204a. Alternatively, the signal lines can be shared as well, forming an electrical bus.

The two cables 205a, 205a can be part of a single cable or can be separate cables 205a, 205b. As a single cable 205, in one embodiment, the cable 205a, 205b can connect to the acoustic sensor 204a via a single connector. As separate cables, in one embodiment, the cable 205b can be connected to a first port on the acoustic sensor 204a and the cable 205a can be coupled to a second port on the acoustic sensor 204a.

FIG. 2B further illustrates an embodiment of the cable 205 in the context of a standalone patient monitoring system 200B. In the standalone patient monitoring system 200B, a blood pressure device 210b is provided that includes a patient monitor 216b disposed on a cuff 212b. The patient monitor 216b includes a display 219 for outputting physiological parameter measurements, trends, waveforms, patient data, and optionally other data for presentation to a clinician. The display 219 can be an LCD display, for example, with a touch screen or the like. The patient monitor 216b can act as a standalone device, not needing to communicate with other devices to process and measure physiological parameters. In some embodiments, the patient monitor 216b can also include any of the wireless functionality described above.

The patient monitor 216b can be integrated into the cuff 212b or can be detachable from the cuff 212b. In one embodiment, the patient monitor 216b can be a readily available mobile computing device with a patient monitoring software application. For example, the patient monitor 216b can be a smart phone, personal digital assistant (PDA), or other wireless device. The patient monitoring software application on the device can perform any of a variety of functions, such as calculating physiological parameters, displaying physiological data, documenting physiological data, and/or wirelessly transmitting physiological data (including measurements or uncalculated raw sensor data) via email, text message (e.g., SMS or MMS), or some other communication medium. Moreover, any of the wireless transceivers or patient monitors described herein can be substituted with such a mobile computing device.

In the depicted embodiment, the patient monitor 216b is connected to three different types of sensors. An optical sensor 202b, coupled to a patient's 201 finger, is connected to the patient monitor 216b via a cable 207. In addition, an acoustic sensor 204b and an electrocardiograph (ECG) sensor 206 are attached to the patient monitor 206b via the cable 205. The optical sensor 202b can perform any of the optical sensor functions described above. Likewise, the acoustic sensor 204b can perform any of the acoustic sensor functions described above. The ECG sensor 206 can be used to monitor electrical activity of the patient's 201 heart.

Advantageously, in the depicted embodiment, the ECG sensor 206 is a bundle sensor that includes one or more ECG leads 208 in a single package. For example, the ECG sensor 206 can include one, two, or three or more leads. One or more of the leads 208 can be an active lead or leads, while another lead 208 can be a reference lead. Other configurations are possible with additional leads within the same package or at different points on the patient's body. Using a bundle ECG sensor 206 can advantageously enable a single cable connection via the cable 205 to the cuff 212b. Similarly, an acoustical sensor can be included in the ECG sensor 206 to advantageously reduce the overall complexity of the on-body assembly.

The cable 205 in FIG. 2B can connect two sensors to the cuff 212b, namely the ECG sensor 206 and the acoustic sensor 204b. Although not shown, the cable 205 can further connect an optical ear sensor to the acoustic sensor 204b in some embodiments, optionally replacing the finger optical sensor 202b. The cable 205 shown in FIG. 2B can have all the features described above with respect to FIG. 2A.

Although not shown, in some embodiments, any of the sensors, cuffs, wireless sensors, or patient monitors described herein can include one or more accelerometers or other motion measurement devices (such as gyroscopes). For example, in FIG. 2B, one or more of the acoustic sensor 204b, the ECG sensor 206, the cuff 212b, the patient monitor 216b, and/or the optical sensor 202b can include one or more motion measurement devices. A motion measurement device can be used by a processor (such as in the patient monitor 216b or other device) to determine motion and/or position of a patient. For example, a motion measurement device can be used to determine whether a patient is sitting up, lying down, walking, or the like.

Movement and/or position data obtained from a motion measurement device can be used to adjust a parameter calculation algorithm to compensate for the patient's motion. For example, a parameter measurement algorithm that compensates for motion can more aggressively compensate for motion in response to high degree of measured movement. When less motion is detected, the algorithm can compensate less aggressively. Movement and/or position data can also be used as a contributing factor to adjusting parameter measurements. Blood pressure, for instance, can change during patient motion due to changes in blood flow. If the patient is detected to be moving, the patient's calculated blood pressure (or other parameter) can therefore be adjusted differently than when the patient is detected to be sitting.

A database can be assembled that includes movement and parameter data (raw or measured parameters) for one or more patients over time. The database can be analyzed by a processor to detect trends that can be used to perform parameter calculation adjustments based on motion or position. Many other variations and uses of the motion and/or position data are possible.

Although the patient monitoring systems described herein, including the systems 100A, 100B, 200A, and 200B have been described in the context of blood pressure cuffs, blood pressure need not be measured in some embodiments. For example, the cuff can be a holder for the patient monitoring devices and/or wireless transceivers and not include any blood pressure measuring functionality. Further, the patient monitoring devices and/or wireless transceivers shown need not be coupled to the patient via a cuff, but can be coupled to the patient at any other location, including not at all. For example, the devices can be coupled to the patient's belt (see FIGS. 3A and 3B), can be carried by the patient (e.g., via a shoulder strap or handle), or can be placed on the patient's bed next to the patient, among other possible locations.

Additionally, various features shown in FIGS. 2A and 2B can be changed or omitted. For instance, the wireless transceiver 216 can be attached to the cuff 212 without the use of the pocket 214. For example, the wireless transceiver can be sown, glued, buttoned or otherwise attached to the cuff using any various known attachment mechanisms. Or, the wireless transceiver 216 can be directly coupled to the patient (e.g., via an armband) and the cuff 212 can be omitted entirely. Instead of a cuff, the wireless transceiver 216 can be coupled to a non-occlusive blood pressure device. Many other configurations are possible.

Figure 3A:
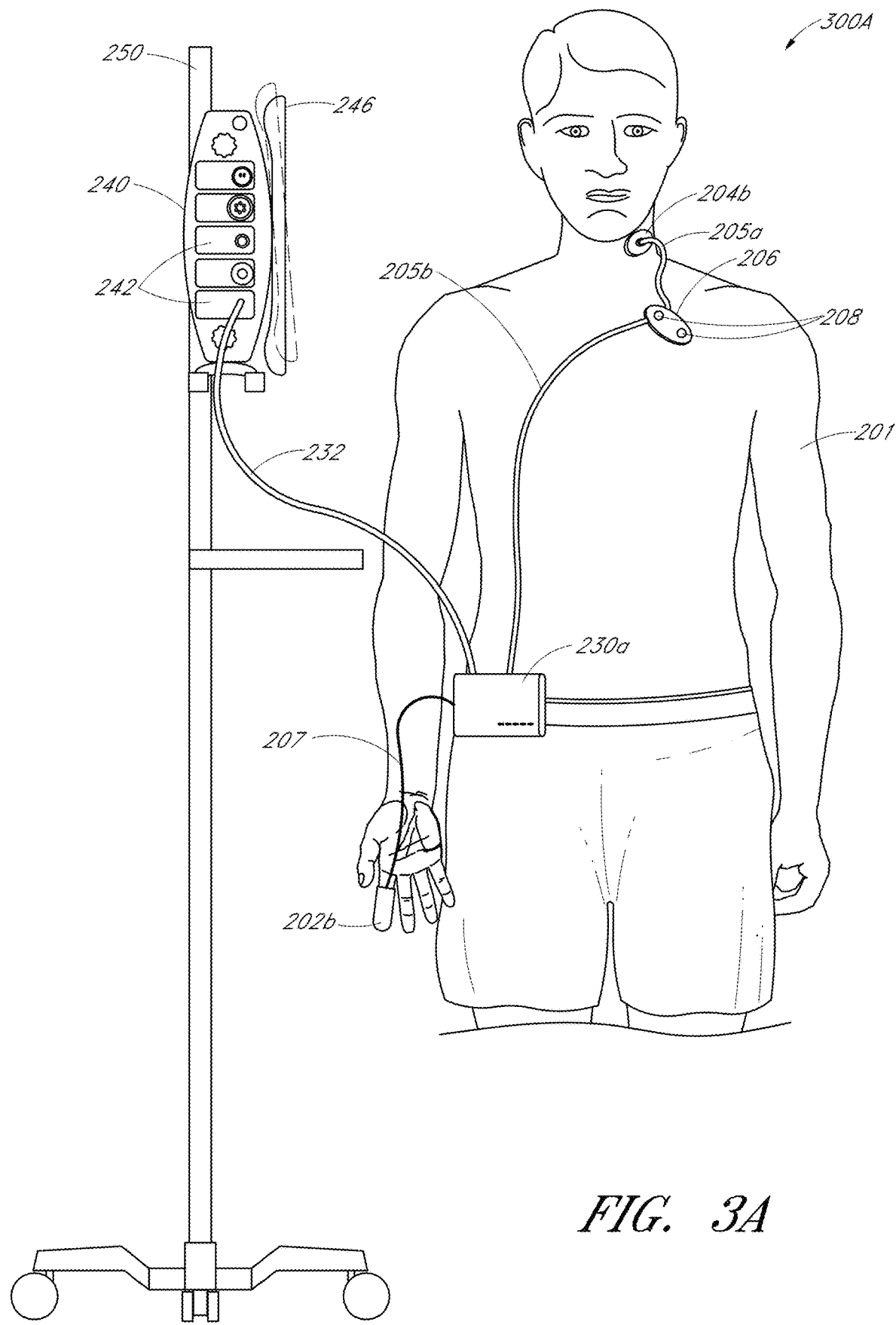
FIGS. 3A and 3B illustrates additional embodiment of patient monitoring systems.
Figure 3B:
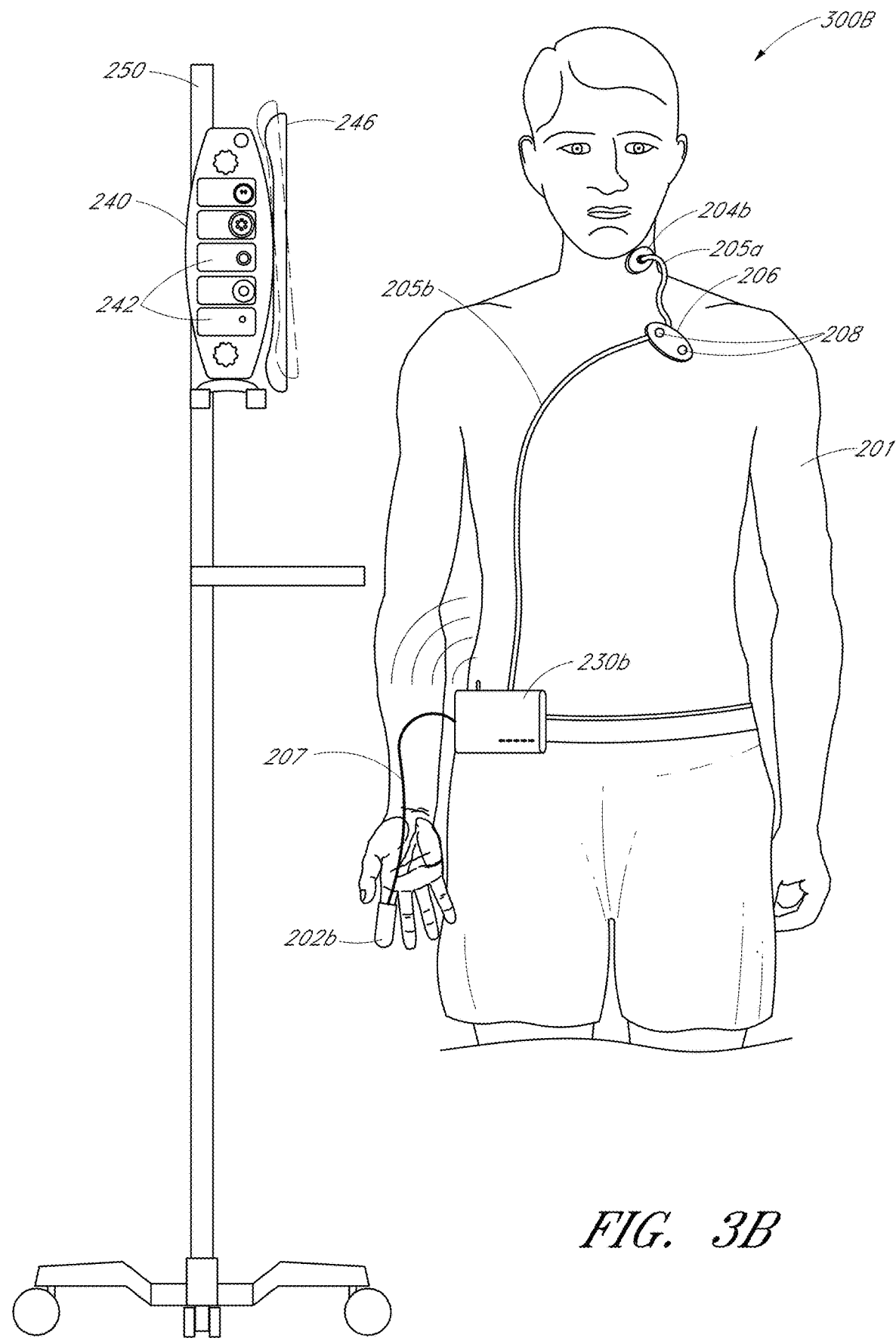

FIGS. 3A and 3B illustrate further embodiments of a patient monitoring system 300A, 300B having a single cable connecting multiple sensors. FIG. 3A depicts a tethered patient monitoring system 300A, while FIG. 3B depicts a wireless patient monitoring system 300B. The patient monitoring systems 300A, 300B illustrate example embodiments where a single cable 305 can be used to connect multiple sensors, without using a blood pressure cuff.

Referring to FIG. 3A, the acoustic and ECG sensors 204b, 206 of FIG. 2 are again shown coupled to the patient 201. As above, these sensors 204b, 206 are coupled together via a cable 205. However, the cable 250 is coupled to a junction device 230a instead of to a blood pressure cuff. In addition, the optical sensor 202b is coupled to the patient 201 and to the junction device 230a via a cable 207. The junction device 230a can anchor the cable 205b to the patient 201 (such as via the patient's belt) and pass through any signals received from the sensors 202b, 204b, 206 to a patient monitor 240 via a single cable 232.

In some embodiments, however, the junction device 230a can include at least some front-end signal processing circuitry. In other embodiments, the junction device 230a also includes a processor for processing physiological parameter measurements. Further, the junction device 230a can include all the features of the patient monitor 216b in some embodiments, such as providing a display that outputs parameters measured from data obtained by the sensors 202b, 204b, 206.

In the depicted embodiment, the patient monitor 240 is connected to a medical stand 250. The patient monitor 240 includes parameter measuring modules 242, one of which is connected to the junction device 230a via the cable 232. The patient monitor 240 further includes a display 246. The display 246 is a user-rotatable display in the depicted embodiment.

Referring to FIG. 3B, the patient monitoring system 300B includes nearly identical features to the patient monitoring system 300A. However, the junction device 230b includes wireless capability, enabling the junction device 230b to wirelessly communicate with the patient monitor 240 and/or other devices.

Figure 4A:
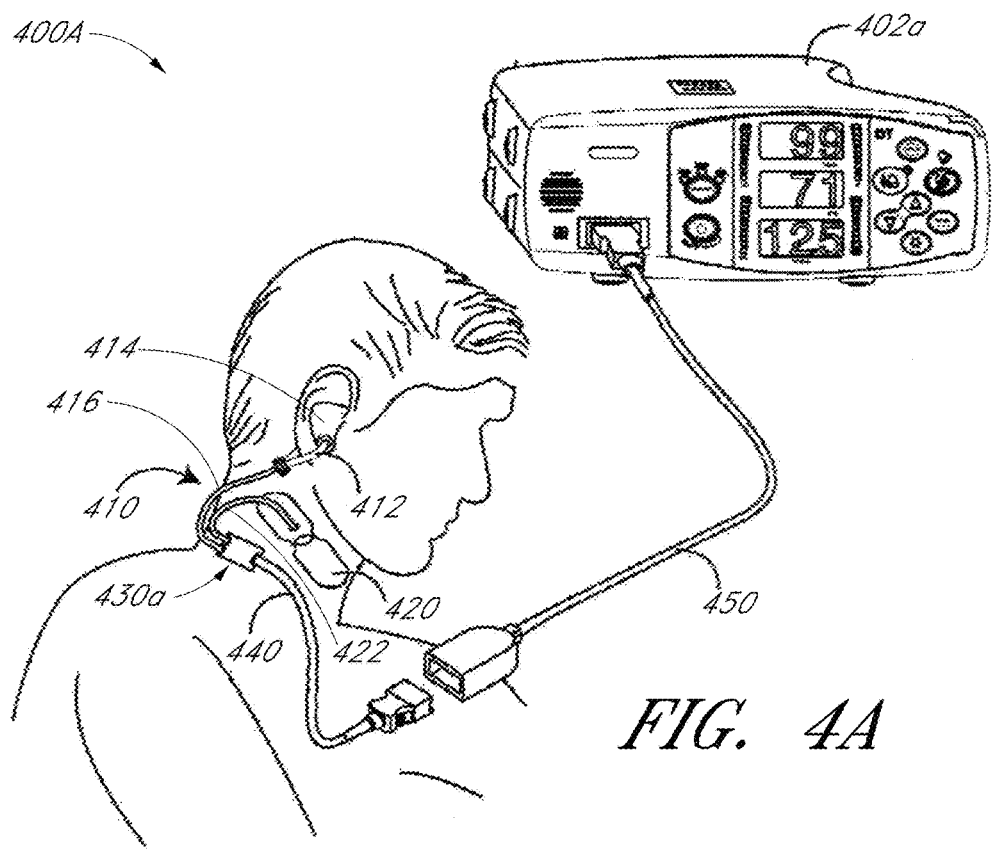
FIGS. 4A and 4B illustrate embodiments of an optical ear sensor and an acoustic sensor connected via a single cable connection system.
Figure 4B:
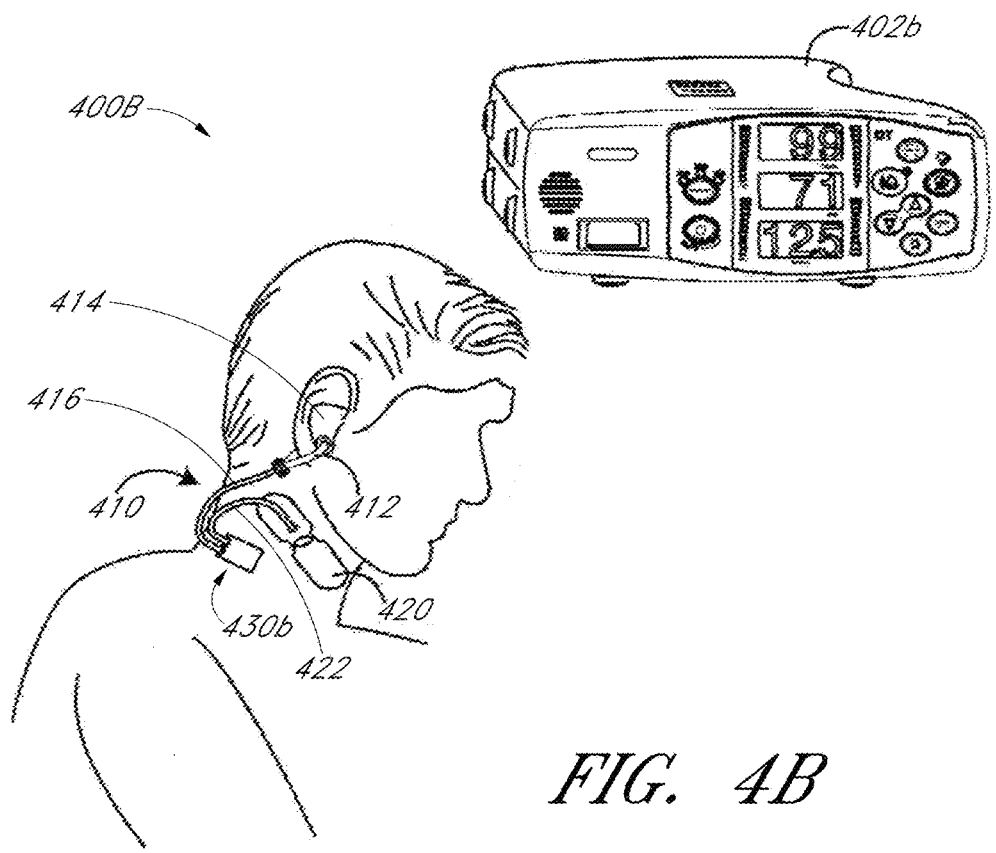

FIGS. 4A and 4B illustrate embodiments of patient monitoring systems 400A, 400B that depict alternative cable connection systems 410 for connecting sensors to a patient monitor 402. Like the cable 205 described above, these cable connection systems 410 can advantageously enhance patient mobility and comfort.

Referring to FIG. 4A, the patient monitoring system 400A includes a patient monitor 402a that measures physiological parameters based on signals obtained from sensors 412, 420 coupled to a patient. These sensors include an optical ear sensor 412 and an acoustic sensor 420 in the embodiment shown. The optical ear sensor 412 can include any of the features of the optical sensors described above. Likewise, the acoustic sensor 420 can include any of the features of the acoustic sensors described above.

The optical ear sensor 412 can be shaped to conform to the cartilaginous structures of the ear, such that the cartilaginous structures can provide additional support to the sensor 412, providing a more secure connection. This connection can be particularly beneficial for monitoring during pre-hospital and emergency use where the patient can move or be moved. In some embodiments, the optical ear sensor 412 can have any of the features described in U.S. application Ser. No. 12/658,872, filed Feb. 16, 2010, entitled "Ear Sensor," the disclosure of which is hereby incorporated by reference in its entirety.

An instrument cable 450 connects the patient monitor 402a to the cable connection system 410. The cable connection system 410 includes a sensor cable 440 connected to the instrument cable 250. The sensor cable 440 is bifurcated into two cable sections 416, 422, which connect to the individual sensors 412, 420 respectively. An anchor 430a connects the sensor cable 440 and cable sections 416, 422. The anchor 430a can include an adhesive for anchoring the cable connection system 410 to the patient, so as to reduce noise from cable movement or the like. Advantageously, the cable connection system 410 can reduce the number and size of cables connecting the patient to a patient monitor 402a. The cable connection system 410 can also be used to connect with any of the other sensors, patient-worn monitors, or wireless devices described above.

FIG. 4B illustrates the patient monitoring system 400B, which includes many of the features of the monitoring system 400A. For example, an optical ear sensor 412 and an acoustic sensor 420 are coupled to the patient. Likewise, the cable connection system 410 is shown, including the cable sections 416, 422 coupled to an anchor 430b. In the depicted embodiment, the cable connection system 410 communicates wirelessly with a patient monitor 402b. For example, the anchor 430b can include a wireless transceiver, or a separate wireless dongle or other device (not shown) can couple to the anchor 430b. The anchor 430b can be connected to a blood pressure cuff, wireless transceiver, junction device, or other device in some embodiments.

Figure 5:
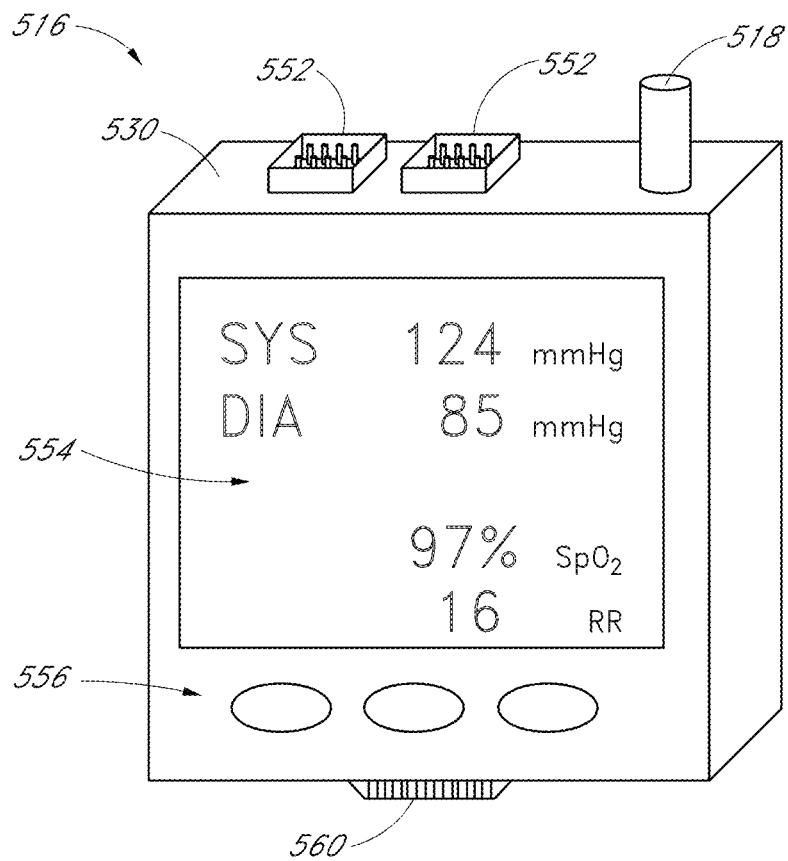
FIG. 5 illustrates an embodiment of a wireless transceiver that can be used with any of the patient monitoring systems described above.

FIG. 5 illustrates a more detailed embodiment of a wireless transceiver 516. The wireless transceiver 516 can have all of the features of the wireless transceiver 516 described above. For example, the wireless transceiver 516 can connect to a blood pressure cuff and to one or more physiological sensors, and the transceiver 516 can transmit sensor data to a wireless receiver.

The depicted embodiment of the transceiver 516 includes a housing 530, which includes connectors 552 for sensor cables (e.g., for optical, acoustic, ECG, and/or other sensors) and a connector 560 for attachment to a blood pressure cuff or other patient-wearable device. The transceiver 516 further includes an antenna 518, which although shown as an external antenna, can be internal in some implementations.

In addition, the transceiver 516 includes a display 554 that depicts values of various parameters, such as systolic and diastolic blood pressure, $SpO_2$, and respiratory rate (RR). The display 554 can also display trends, alarms, and the like. The transceiver 516 can be implemented with the display 554 in embodiments where the transceiver 516 also acts as a patient monitor. The transceiver 516 further includes controls 556, which can be used to manipulate settings and functions of the transceiver 516.

FIGS. 6A through 6C illustrate embodiments of wireless patient monitoring systems 600. FIG. 6A illustrates a patient monitoring system 600A that includes a wireless transceiver 616, which can include the features of any of the transceivers 216, 216 described above. The transceiver 616 provides a wireless signal over a wireless link 612 to a patient monitor 620. The wireless signal can include physiological information obtained from one or more sensors, physiological information that has been front-end processed by the transceiver 616, or the like.

The patient monitor 620 can act as the wireless receiver 220 of FIG. 2. The patient monitor 620 can process the wireless signal received from the transceiver 616 to obtain values, waveforms, and the like for one or more physiological parameters. The patient monitor 620 can perform any of the patient monitoring functions described above with respect to FIGS. 2 through 5.

In addition, the patient monitor 620 can provide at least some of the physiological information received from the transceiver 616 to a multi-patient monitoring system (MMS) 640 over a network 630. The MMS 640 can include one or more physical computing devices, such as servers, having hardware and/or software for providing the physiological information to other devices in the network 630. For example, the MMS 640 can use standardized protocols (such as TCP/IP) or proprietary protocols to communicate the physiological information to one or more nurses' station computers (not shown) and/or clinician devices (not shown) via the network 630. In one embodiment, the MMS 640 can include some or all the features of the MMS described in U.S. Publication No. 2008/0188760, referred to above.

The network 630 can be a LAN or WAN, wireless LAN ("WLAN"), or other type of network used in any hospital, nursing home, patient care center, or other clinical location. In some implementations, the network 210 can interconnect devices from multiple hospitals or clinical locations, which can be remote from one another, through the Internet, one or more Intranets, a leased line, or the like. Thus, the MMS 640 can advantageously distribute the physiological information to a variety of devices that are geographically co-located or geographically separated.

FIG. 6B illustrates another embodiment of a patient monitoring system 600B, where the transceiver 616 transmits physiological information to a base station 624 via the wireless link 612. In this embodiment, the transceiver 616 can perform the functions of a patient monitor, such as any of the patient monitor functions described above. The transceiver 616 can provide processed sensor signals to the base station 624, which forwards the information on to the MMS 640 over the network 630.

FIG. 6C illustrates yet another embodiment of a patient monitoring system 600B, where the transceiver 616 transmits physiological information directly to the MMS 640. The MMS 640 can include wireless receiver functionality, for example. Thus, the embodiments shown in FIGS. 6A through 6C illustrate that the transceiver 616 can communicate with a variety of different types of devices.

Figure 7:
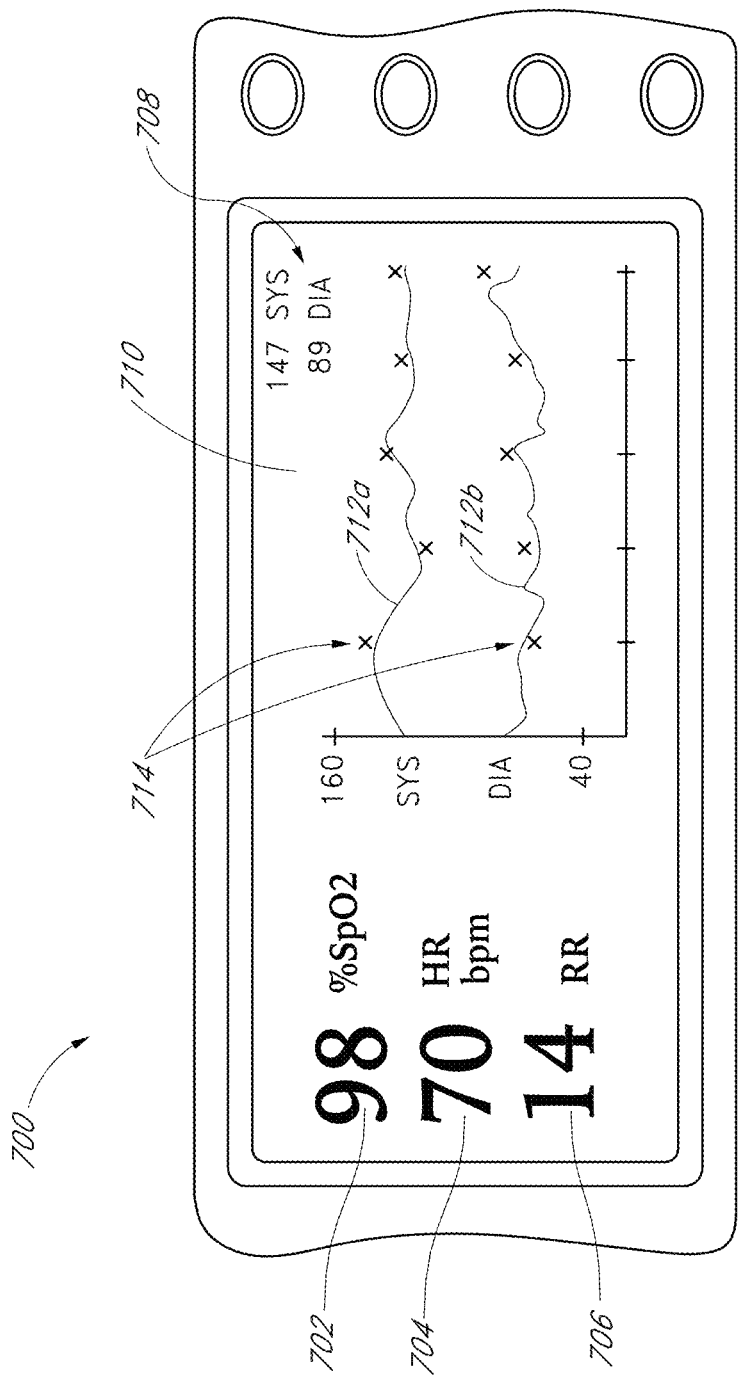
FIG. 7 illustrates an embodiment of a physiological parameter display that can be used with any of the patient monitoring systems described above.

FIG. 7 illustrates an embodiment of a physiological parameter display 700. The physiological parameter display 700 can be output by any of the systems described above. For instance, the physiological parameter display 700 can be output by any of the wireless receivers, transceivers, or patient monitors described above. Advantageously, in certain embodiments, the physiological parameter display 700 can display multiple parameters, including noninvasive blood pressure (NIBP) obtained using both oscillometric and non-oscillometric techniques.

The physiological parameter display 700 can display any of the physiological parameters described above, to name a few. In the depicted embodiment, the physiological parameter display 700 is shown displaying oxygen saturation 702, heart rate 704, and respiratory rate 706. In addition, the physiological parameter display 700 displays blood pressure 708, including systolic and diastolic blood pressure.

The display 700 further shows a plot 710 of continuous or substantially continuous blood pressure values measured over time. The plot 710 includes a trace 712a for systolic pressure and a trace 712b for diastolic pressure. The traces 712a, 712b can be generated using a variety of devices and techniques. For instance, the traces 712a, 712b can be generated using any of the velocity-based continuous blood pressure measurement techniques described above and described in further detail in U.S. Pat. Nos. 5,590,649 and 5,785,659, referred to above.

Periodically, oscillometric blood pressure measurements (sometimes referred to as Gold Standard NIBP) can be taken, using any of the cuffs described above. These measurements are shown by markers 714 on the plot 710. By way of illustration, the markers 714 are "X's" in the depicted embodiment, but the type of marker 714 used can be different in other implementations. In certain embodiments, oscillometric blood pressure measurements are taken at predefined intervals, resulting in the measurements shown by the markers 714.

In addition to or instead of taking these measurements at intervals, oscillometric blood pressure measurements can be triggered using ICI techniques, e.g., based at least partly on an analysis of the noninvasive blood pressure measurements indicated by the traces 712a, 712b. Advantageously, by showing both types of noninvasive blood pressure measurements in the plot 710, the display 700 can provide a clinician with continuous and oscillometric blood pressure information.

Figure 8:
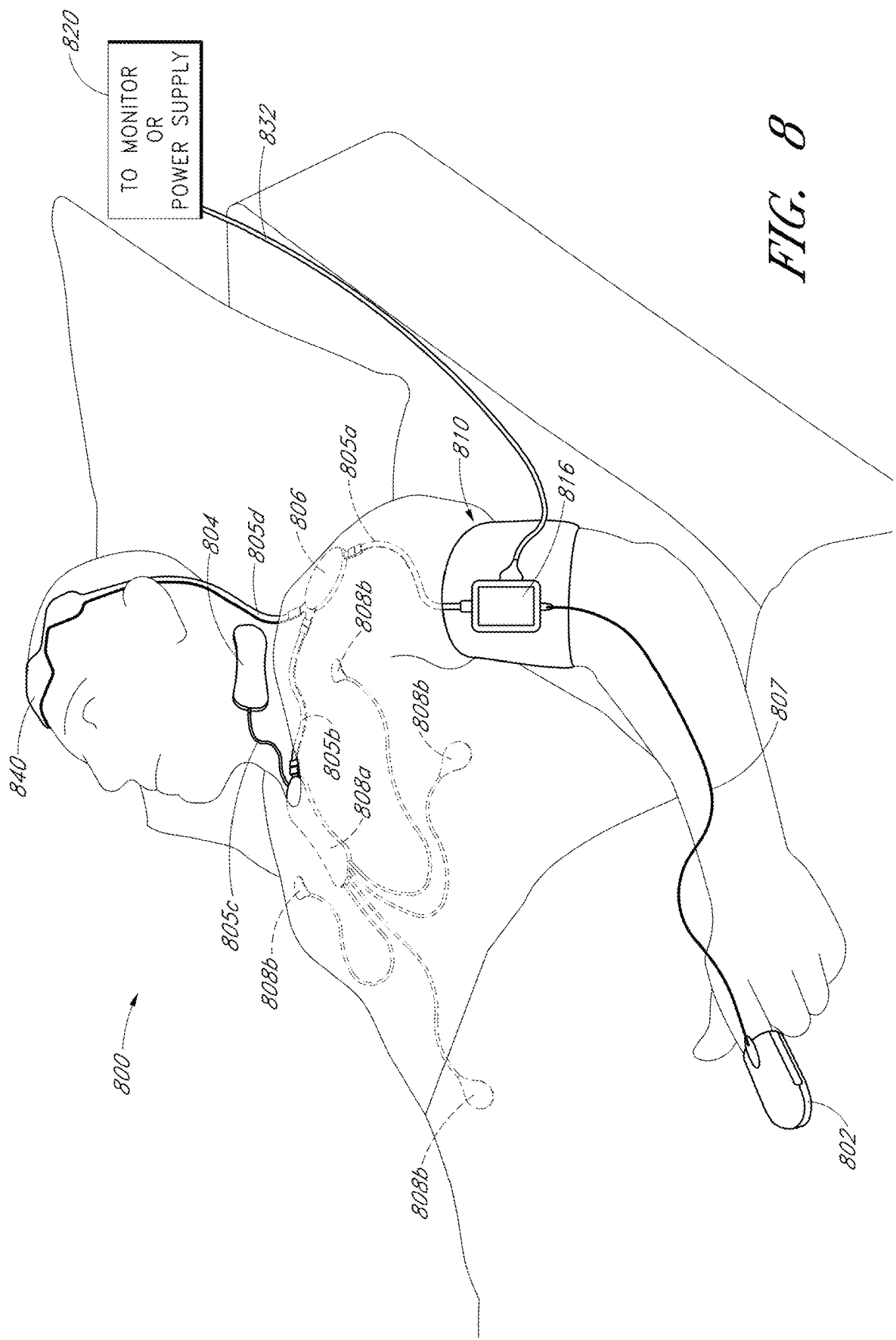
FIG. 8 illustrates a further embodiment of a patient monitoring system.

FIG. 8 illustrates another embodiment of a patient monitoring system 800. The features of the patient monitoring system 800 can be combined with any of the features of the systems described above. Likewise, any of the features described above can be incorporated into the patient monitoring system 800. Advantageously, in the depicted embodiment, the patient monitoring system 800 includes a cable hub 806 that enables one or many sensors to be selectively connected and disconnected to the cable hub 806.

Like the patient monitoring systems described above, the monitoring system 800 includes a cuff 810 with a patient device 816 for providing physiological information to a monitor 820 or which can receive power from a power supply (820). The cuff 810 can be a blood pressure cuff or merely a holder for the patient device 816. The patient device 816 can instead be a wireless transceiver having all the features of the wireless devices described above.

The patient device 816 is in coupled with an optical finger sensor 802 via cable 807. Further, the patient device 816 is coupled with the cable hub 806 via a cable 805a. The cable hub 806 can be selectively connected to one or more sensors. In the depicted embodiment, example sensors shown coupled to the cable hub 806 include an ECG sensor 808a and a brain sensor 840. The ECG sensor 808a can be single-lead or multi-lead sensor. The brain sensor 840 can be an electroencephalography (EEG) sensor and/or an optical sensor. An example of EEG sensor that can be used as the brain sensor 840 is the SEDLine™ sensor available from Masimo® Corporation of Irvine, Calif., which can be used for depth-of-anesthesia monitoring among other uses. Optical brain sensors can perform spectrophotometric measurements using, for example, reflectance pulse oximetry. The brain sensor 840 can incorporate both an EEG/depth-of-anesthesia sensor and an optical sensor for cerebral oximetry.

The ECG sensor 808a is coupled to an acoustic sensor 804 and one or more additional ECG leads 808b. For illustrative purposes, four additional leads 808b are shown, for a 5-lead ECG configuration. In other embodiments, one or two additional leads 808b are used instead of four additional leads. In still other embodiments, up to at least 12 leads 808b can be included. Acoustic sensors can also be disposed in the ECG sensor 808a and/or lead(s) 808b or on other locations of the body, such as over a patient's stomach (e.g., to detect bowel sounds, thereby verifying patient's digestive health, for example, in preparation for discharge from a hospital). Further, in other embodiments, the acoustic sensor 804 can connect directly to the cable hub 806 instead of to the ECG sensor 808a.

As mentioned above, the cable hub 806 can enable one or many sensors to be selectively connected and disconnected to the cable hub 806. This configurability aspect of the cable hub 806 can allow different sensors to be attached or removed from a patient based on the patient's monitoring needs, without coupling new cables to the monitor 820. Instead, a single, light-weight cable 832 couples to the monitor 820 in certain embodiments, or wireless technology can be used to communicate with the monitor 820 (see, e.g., FIG. 1). A patient's monitoring needs can change as the patient is moved from one area of a care facility to another, such as from an operating room or intensive care unit to a general floor. The cable configuration shown, including the cable hub 806, can allow the patient to be disconnected from a single cable to the monitor 820 and easily moved to another room, where a new monitor can be coupled to the patient. Of course, the monitor 820 may move with the patient from room to room, but the single cable connection 832 rather than several can facilitate easier patient transport.

Further, in other embodiments, the cuff 810 and/or patient device 816 need not be included, but the cable hub 806 can instead connect directly to the monitor wirelessly or via a cable. Additionally, the cable hub 806 or the patient device 816 may include electronics for front-end processing, digitizing, or signal processing for one or more sensors. Placing front-end signal conditioning and/or analog-to-digital conversion circuitry in one or more of these devices can make it possible to send continuous waveforms wirelessly and/or allow for a small, more user-friendly wire (and hence cable 832) routing to the monitor 820.

The cable hub 806 can also be attached to the patient via an adhesive, allowing the cable hub 806 to become a wearable component. Together, the various sensors, cables, and cable hub 806 shown can be a complete body-worn patient monitoring system. The body-worn patient monitoring system can communicate with a patient monitor 820 as shown, which can be a tablet, handheld device, a hardware module, or a traditional monitor with a large display, to name a few possible devices.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "may," "might," "could," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated can be made without departing from the spirit of the disclosure. As will be recognized, certain embodiments of the inventions described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

What is claimed is:

1. A wireless patient monitoring system comprising:
a battery;
a plurality of sensors comprising:
an optical sensor configured to obtain photoplethysmographs, the optical sensor including at least one emitter configured to emit light and at least one detector configured to detect said light after attenuation by tissue of a user, said photoplethysmographs obtained based on said detected light;

a blood pressure device configured to be attached to an arm of the user;

an acoustic sensor configured to be attached to a neck of the user;

an anchor configured to be adhered to the user, the anchor configured to electrically couple the blood pressure device and the acoustic sensor;

a first cable connecting the acoustic sensor to the anchor;

a second cable connecting the anchor to the blood pressure device; and a wireless transceiver configured to be mounted to the arm of the user;

the wireless transceiver configured to wirelessly transmit data from said plurality of sensors to a second device for processing into physiological measurements.

2. The system of claim 1, wherein the wireless transceiver is configured to perform bandpass filtering.

3. The system of claim 1, wherein the wireless transceiver is configured to perform signal conditioning.

4. The system of claim 1, wherein the wireless transceiver is configured to wirelessly transmit said data over Bluetooth.

5. The system of claim 1, wherein the optical sensor is configured to be coupled to a fingertip.

6. The system of claim 1, further comprising an adhesive for attaching the optical sensor to skin of the user.

7. The system of claim 1, further comprising a band configured to secure the system to the user.

8. A system comprising:
a sensor assembly comprising:
a battery;
a plurality of sensors comprising:
an optical sensor configured to obtain photoplethysmographs, the optical sensor including at least one emitter configured to emit light and at least one detector configured to detect said light after attenuation by tissue of a user, said photoplethysmographs obtained based on said detected light;

a blood pressure device configured to be attached to an arm of the user;

an acoustic sensor configured to be attached to a neck of the user;

an anchor configured to be adhered to the user at a location spaced apart from the acoustic sensor, the anchor configured to electrically couple the blood pressure device and the acoustic sensor;

a wireless transceiver configured to wirelessly transmit data from the plurality of sensors to a second device; and the second device comprising a processor, a memory, and a display, the memory storing computer-executable instructions that, when executed, cause the second device to:

process said data received from the sensor assembly to determine one or more physiological measurements;

display the one or more physiological measurements on the display.

9. The system of claim 8, wherein the wireless transceiver is configured to perform bandpass filtering.

10. The system of claim 8, wherein the wireless transceiver is configured to perform signal conditioning.

11. The system of claim 8, wherein, when executed, the computer-executable instructions cause the second device to display a trend in said one or more physiological measurements on the display.

12. The system of claim 8, wherein, when executed, the computer-executable instructions cause the second device to assemble a database including said one or more physiological measurements.

13. The system of claim 1, wherein the blood pressure device is electronically actuated based on a time interval.

14. The system of claim 1, wherein the wireless transceiver is configured to wirelessly transmit said data over Wi-Fi.

* * * * *